(12) United States Patent
Roh et al.

(10) Patent No.: US 11,234,478 B2
(45) Date of Patent: Feb. 1, 2022

(54) INSOLE AND SHOES COMPRISING THE SAME

(71) Applicant: Samsung Electronics Co., Ltd., Suwon-si (KR)

(72) Inventors: Se-Gon Roh, Suwon-si (KR); Changhyun Roh, Seongnam-si (KR); Youngbo Shim, Seoul (KR); Byung-Kwon Choi, Suwon-si (KR); Haewook Ahn, Seoul (KR); Mikyung Park, Seoul (KR); Yeiji Bae, Seoul (KR); Minho Choi, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 31 days.

(21) Appl. No.: 16/433,435

(22) Filed: Jun. 6, 2019

(65) Prior Publication Data

US 2020/0060379 A1 Feb. 27, 2020

(30) Foreign Application Priority Data

Aug. 27, 2018 (KR) ........................ 10-2018-0100345

(51) Int. Cl.
*A43B 3/00* (2006.01)
*A43B 17/18* (2006.01)

(52) U.S. Cl.
CPC ............ *A43B 3/0005* (2013.01); *A43B 17/18* (2013.01); *A61H 2201/164* (2013.01); *A61H 2201/165* (2013.01); *A61H 2205/12* (2013.01)

(58) Field of Classification Search
CPC ..... A43B 3/0005; A43B 17/18; A43B 3/0015; A43B 3/001; A43B 3/0021; A43B 17/00; A61B 1/1038; A61B 5/1104; A61B 5/6807; A61B 5/112; A61H 2201/164; A61H 2201/165; A61H 2201/12; A61H 3/00
USPC ....................................................... 36/43, 44
See application file for complete search history.

(56) References Cited

U.S. PATENT DOCUMENTS

| | | |
|---|---|---|
| 3,505,436 A | 4/1970 | Rutsch |
| 4,745,930 A | 5/1988 | Confer |
| 5,913,838 A | 6/1999 | Reilly |
| 6,195,921 B1 | 3/2001 | Truong |

(Continued)

FOREIGN PATENT DOCUMENTS

| | | |
|---|---|---|
| CN | 201256658 Y | 6/2009 |
| CN | 102499859 A | 6/2012 |

(Continued)

OTHER PUBLICATIONS

Final Office Action dated Jan. 17, 2020 for U.S. Appl. No. 15/403,546.

(Continued)

*Primary Examiner* — F Griffin Hall
(74) *Attorney, Agent, or Firm* — Harness, Dickey & Pierce, P.L.C.

(57) ABSTRACT

An insole may include an insole body in a shape receivable in a shoe; an electronic element provided in the insole body; a connection line configured to electrically connect to the electronic element and including a contact terminal exposed to the outside of the insole body; and a connector including a detachable member configured to at least partially protrude outward from the insole body and configured to support the contact terminal.

18 Claims, 21 Drawing Sheets

(56) References Cited

U.S. PATENT DOCUMENTS

| | | |
|---|---|---|
| 6,978,684 B2 | 12/2005 | Nurse |
| 7,997,007 B2 | 8/2011 | Sanabria-Hernandez |
| 8,056,268 B2 | 11/2011 | DiBenedetto et al. |
| 8,308,665 B2 | 11/2012 | Harry et al. |
| 8,350,671 B2 | 1/2013 | Kim |
| 8,641,220 B1 | 2/2014 | Lin |
| 9,135,792 B2 | 9/2015 | Han et al. |
| 9,549,585 B2 | 1/2017 | Amos et al. |
| 10,595,749 B1 | 3/2020 | Javitt et al. |
| 2006/0103538 A1 | 5/2006 | Daniel |
| 2007/0159507 A1 | 7/2007 | Urano |
| 2009/0200880 A1 | 8/2009 | Mortimer et al. |
| 2011/0107771 A1 | 5/2011 | Crist et al. |
| 2011/0153197 A1 | 6/2011 | Song |
| 2011/0271554 A1 | 11/2011 | Jazdanian |
| 2012/0023785 A1 | 2/2012 | Barnes et al. |
| 2012/0186101 A1 | 7/2012 | Sanchez |
| 2012/0222333 A1 | 9/2012 | Short et al. |
| 2012/0291564 A1 | 11/2012 | Amos et al. |
| 2013/0072835 A1 | 3/2013 | Harry et al. |
| 2013/0213147 A1* | 8/2013 | Rice ................... A43B 7/088 73/862.046 |
| 2014/0142475 A1 | 5/2014 | Goldfarb et al. |
| 2014/0316309 A1 | 10/2014 | Seo et al. |
| 2015/0321339 A1 | 11/2015 | Asbeck et al. |
| 2016/0012687 A1 | 1/2016 | Obana et al. |
| 2016/0206499 A1 | 7/2016 | Shim et al. |
| 2016/0206503 A1 | 7/2016 | Planke |
| 2016/0324445 A1 | 11/2016 | Kim et al. |
| 2016/0324487 A1 | 11/2016 | Guo et al. |
| 2016/0345679 A1 | 12/2016 | Beers et al. |
| 2016/0366266 A1* | 12/2016 | Chung ................. H04W 76/14 |
| 2017/0112712 A1 | 4/2017 | Chawan et al. |
| 2017/0156659 A1 | 6/2017 | Yang et al. |
| 2017/0156662 A1 | 6/2017 | Goodall et al. |
| 2017/0217062 A1 | 8/2017 | Bae |
| 2017/0265594 A1 | 9/2017 | Walker et al. |
| 2018/0020764 A1 | 1/2018 | Walker |
| 2018/0085281 A1 | 3/2018 | Roh |
| 2018/0168283 A1 | 6/2018 | Agati |
| 2018/0168913 A1 | 6/2018 | Sedic |
| 2018/0199656 A1 | 7/2018 | Doll |
| 2018/0199674 A1 | 7/2018 | Walker et al. |
| 2018/0200598 A1 | 7/2018 | Guan et al. |
| 2018/0346167 A1 | 12/2018 | Capriotti et al. |
| 2019/0122507 A1 | 4/2019 | Roh |
| 2020/0289028 A1 | 9/2020 | Oumnia |
| 2021/0086721 A1 | 3/2021 | Carraro et al. |

FOREIGN PATENT DOCUMENTS

| | | |
|---|---|---|
| CN | 203105800 U | 8/2013 |
| CN | 106539182 A | 3/2017 |
| DE | 202008008727 U1 | 9/2008 |
| DE | 102014115135 A1 | 4/2015 |
| EP | 1608303 A2 | 12/2005 |
| EP | 3081160 A1 | 10/2016 |
| IN | 230069 | 9/2007 |
| JP | 3151948 B2 | 4/2001 |
| JP | 2006204520 A | 8/2006 |
| JP | 2007268012 A | 10/2007 |
| JP | 2007268056 A | 10/2007 |
| JP | 5189911 B2 | 4/2013 |
| JP | 5741375 B2 | 7/2015 |
| KR | 10-2005-0122205 A | 12/2005 |
| KR | 20050122205 A | 12/2005 |
| KR | 2007-0053911 A | 5/2007 |
| KR | 100946186 B1 | 3/2010 |
| KR | 20120057626 A | 6/2012 |
| KR | 101248190 B1 | 3/2013 |
| KR | 10-1302364 | 9/2013 |
| KR | 101302364 B1 | 9/2013 |
| KR | 101350334 B1 | 1/2014 |
| KR | 101492862 B1 | 2/2015 |
| KR | 20160090088 A | 7/2016 |
| KR | 2017-0143341 A | 12/2017 |
| WO | WO-2008/061420 A1 | 5/2008 |
| WO | WO-2009/039555 A1 | 4/2009 |
| WO | WO-2009105918 A1 | 9/2009 |
| WO | WO-2012/112930 A1 | 8/2012 |
| WO | WO-2015/004498 A1 | 1/2015 |
| WO | WO-2016/191115 A1 | 12/2016 |

OTHER PUBLICATIONS

Extended European Search Report dated Jan. 24, 2020 for European Patent Application No. 19188429.5.

Non-Final Office Action dated Apr. 22, 2019 in U.S. Appl. No. 15/403,546.

Final Office Action dated Aug. 7, 2019 in U.S. Appl. No. 15/403,546.

Non-Final Office Action dated Sep. 18, 2018 in U.S. Appl. No. 15/894,320.

Notice of Allowance dated Mar. 6, 2019 in U.S. Appl. No. 15/894,320.

Non-Final Office Action dated Jul. 22, 2020 for U.S. Appl. No. 16/415,220.

Extended European Search Report dated Feb. 5, 2020 for EP Application No. 19188457.6.

Extended European Search Report dated Mar. 3, 2020 for corresponding European Application No. 19191372.2.

Non-Final Office Action dated Apr. 8, 2020 in U.S. Appl. No. 15/403,546.

U.S. Appl. No. 16/433,435, filed Jun. 6, 2019.

Notice of Allowance dated Dec. 14, 2020 in corresponding U.S. Appl. No. 16/415,220.

U.S. Appl. No. 17/205,270, filed Mar. 18, 2021.

Non-Final Office Action dated Apr. 29, 2021 in related U.S. Appl. No. 16/433,408.

Extended European Search Report dated Jan. 9, 2020 for EP Application No. 19188453.3.

U.S. Appl. No. 15/403,546, filed Jan. 11, 2017.

U.S. Appl. No. 16/415,220, filed May 17, 2019.

U.S. Appl. No. 15/894,320, filed Feb. 12, 2018.

U.S. Appl. No. 16/433,408, filed Jun. 6, 2019.

U.S. Appl. No. 16/433,600, filed Jun. 6, 2019.

Bing Chen et al., "Design of a Lower Extremity Exoskeleton for Motion Assistance in Paralyzed Individuals", Proceedings of the 2015 IEEE Conference on Robotics and Biomimetics, Zhuhai, China, Dec. 6-9, 2015, pp. 144-149.

Slavko Rogan et al., "Stochastic resonance whole-body vibration training for chair rising performance on untrained elderly—A pilot study", Archives of Gerontology and Geriatrics 55 Mar. 2012, pp. 468-473.

Attila A. Priplata et al., "Vibrating insoles and balance control in elderly people", The Lancet, vol. 362, Oct. 4, 2003, pp. 1123-1124, www.thelancet.com.

U.S. Final Office Action dated Oct. 26, 2021 for U.S. Appl. No. 16/433,408.

* cited by examiner

INSOLE AND SHOES COMPRISING THE SAME

CROSS-REFERENCE TO RELATED APPLICATION

This application claims priority under 35 U.S.C. § 119 to Korean Patent Application No. 10-2018-0100345, filed on Aug. 27, 2018, in the Korean Intellectual Property Office, the entire contents of which are incorporated herein by reference in their entirety.

BACKGROUND

1. Field

Some example embodiments relate to an insole and/or shoes including the insole.

2. Description of the Related Art

A user wears shoes in daily life. Shoes protect feet of the user comfortably and safely. In recent years, wearable devices are developed to detect a gait pattern of the user and to assist the user to stably walk by providing a sensor and/or a driver to a shoe.

SUMMARY

Some example embodiments relate to an insole.

In some example embodiments, the insole may include an insole body insertable in a shoe; an electronic element in the insole body; a connection line configured to electrically connect to the electronic element, the connection line including a contact terminal exposed to an outside of the insole body; and a connector including a detachable member configured to at least partially protrude from the insole body towards the outside of the insole body, the connector configured to support the contact terminal.

In some example embodiments, the electronic element includes one or more of a vibrator, a pressure sensor, or an inertial sensor.

In some example embodiments, the insole further includes a support layer in the insole body, the support layer configured to support the electronic element.

In some example embodiments, the connector further includes a base configured to support the contact terminal, and to expose the contact terminal at a portion in which the contact terminal wraps around the base, and wherein the detachable member is configured to protrude downward from the base with respect to a top surface of the insole body.

In some example embodiments, the detachable member includes a left arm protruding from a first side of the base with respect to the top surface of the insole body; and a right arm protruding from a second side of the base with respect to the top surface of the insole body such that the right arm is separated from and faces the left arm.

In some example embodiments, the base includes a lower plate; an upper plate configured to be separated from the lower plate in a vertical direction; and a connection member configured to connect the lower plate and the upper plate.

In some example embodiments, the connection member is in a U shape such that the lower plate is separated from the upper plate.

In some example embodiments, the connection line is configured to attach to a bottom surface of the lower plate with respect to the top surface of the insole body such that the connection line is exposed to the outside of the insole body.

In some example embodiments, the base further includes a plurality of ribs configured to protrude from the lower plate with respect to the top surface of the insole body, the plurality of ribs extending in parallel, and wherein the connection line is between two adjacent ribs among the plurality of ribs.

In some example embodiments, the base includes a fluid through hole therein in a lengthwise direction of the insole body.

In some example embodiments, the electronic element includes a plurality of electronic elements, the plurality of electronic elements including a first front electronic element and a second front electronic element in a front portion of the insole body, the first front electronic element being spaced apart from the second front electronic element in a widthwise direction of the insole body.

In some example embodiments, the electronic element includes a plurality of electronic elements, the plurality of electronic elements including a first rear electronic element and a second rear electronic element in a rear portion of the insole body, the first rear electronic element being spaced apart from the second rear electronic element in a lengthwise direction of the insole body.

Some other example embodiments also relate to a shoe.

In some example embodiments, the shoe includes a midsole including a receiving groove; a control device configured to mount to the receiving groove; and an insole including, an insole body insertable into an upper portion of the midsole, an electronic element in the insole body, a connection line configured to electrically connect to the electronic element, and a connector configured to connect the connection line to the control device.

In some example embodiments, the electronic element includes at least one of a vibrator, a pressure sensor, and an inertial sensor.

In some example embodiments, the insole further includes a support layer in the insole body, the support layer configured to support the electronic element.

In some example embodiments, at least a portion of the connector is configured to protrude from the insole body towards an outside of the insole body.

In some example embodiments, the control device includes a case including a fastening groove configured to receive a portion of the connector; and an access terminal in an upper portion of the case, the access terminal configured to contact the connection line.

In some example embodiments, the access terminal is configured to move in a vertical direction relative to a top surface of the case.

In some example embodiments, the insole body has a groove recessed in a bottom surface of the insole body, the groove having an area less than that of the electronic element.

In some example embodiments, the support layer has a hole therein, and the insole body has a groove recessed in a bottom surface of the insole body, the groove having an area greater than that of the hole.

Some other example embodiments relate to a control assembly.

In some example embodiments, the control assembly includes a control device including a battery and an access terminal; a connection line configured to extend outward from the control device; and a user interface configured to attach to the connection line, and to selectively open an electrical connection between the battery and the access terminal.

In some example embodiments, the user interface includes a power button configured to switch between an ON state and an OFF state, the ON state being a state in which the electrical connection between the battery and the access terminal is unblocked and the OFF state being a state in which the electrical connection between the battery and the access terminal is opened.

In some example embodiments, the user interface further includes a light source configured to indicate whether the power button is in the ON state or the OFF state.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
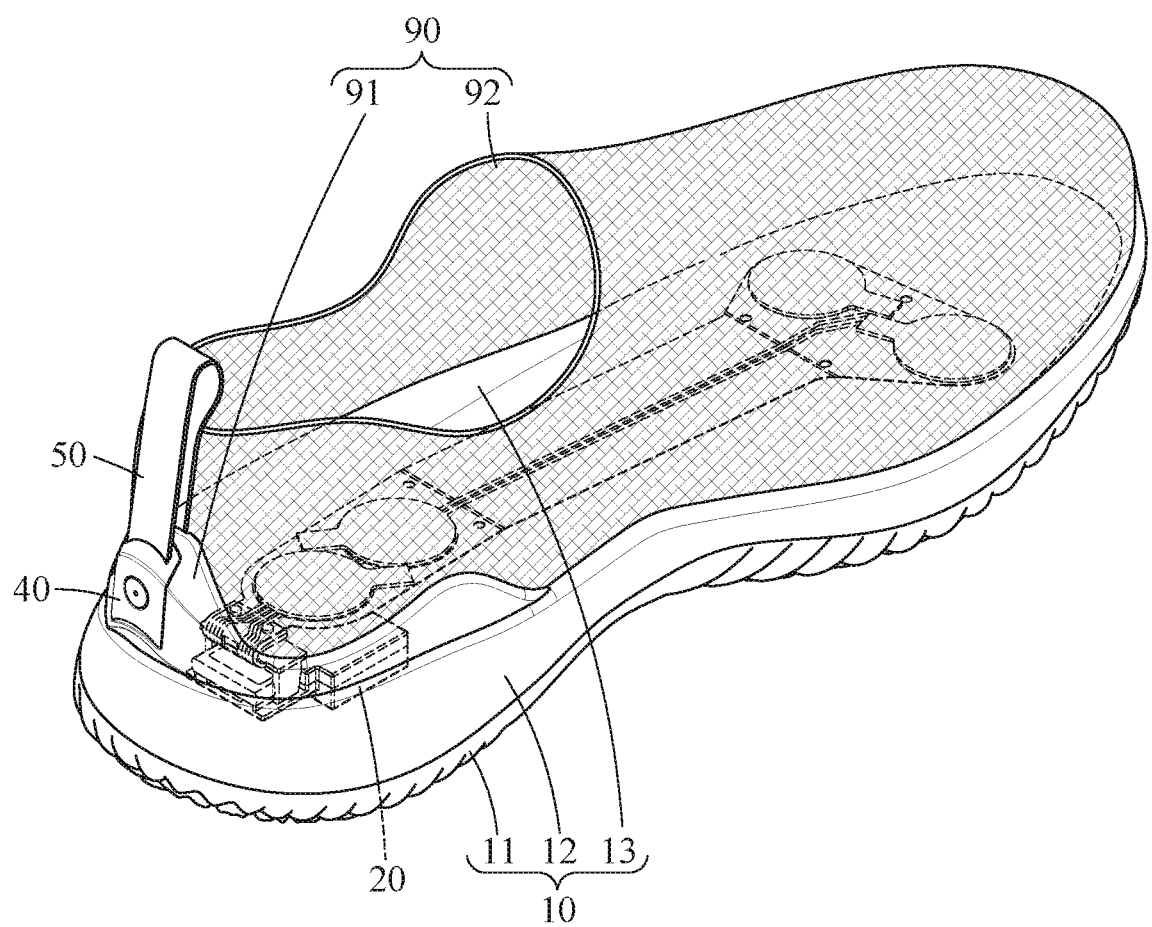
FIG. 1 is a perspective view of a shoe according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit example embodiments to the particular example embodiments disclosed herein. On the contrary, the example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
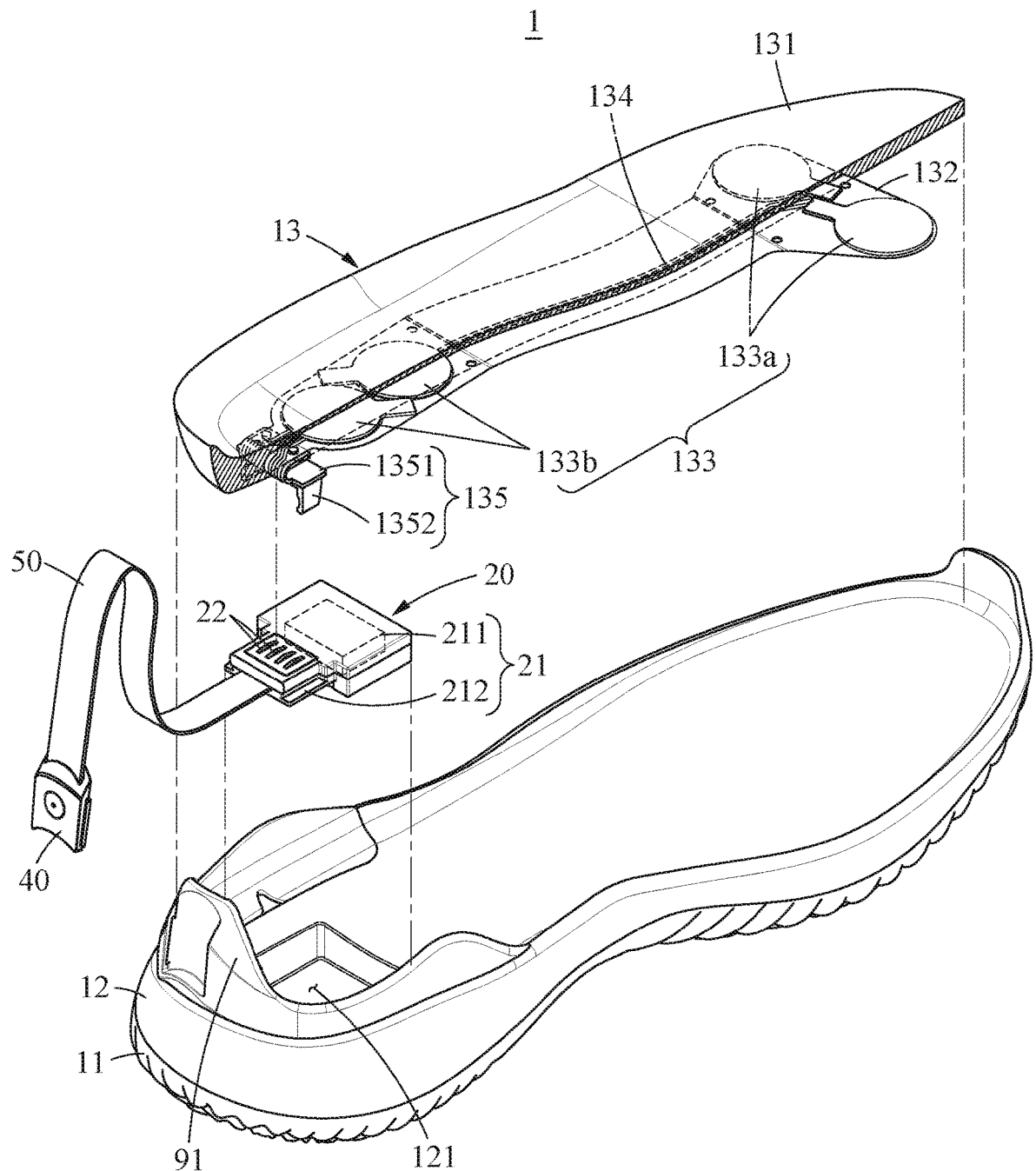
FIG. 2 is an exploded perspective view of a shoe and a partially cut insole body according to at least one example embodiment.
Figure 3:
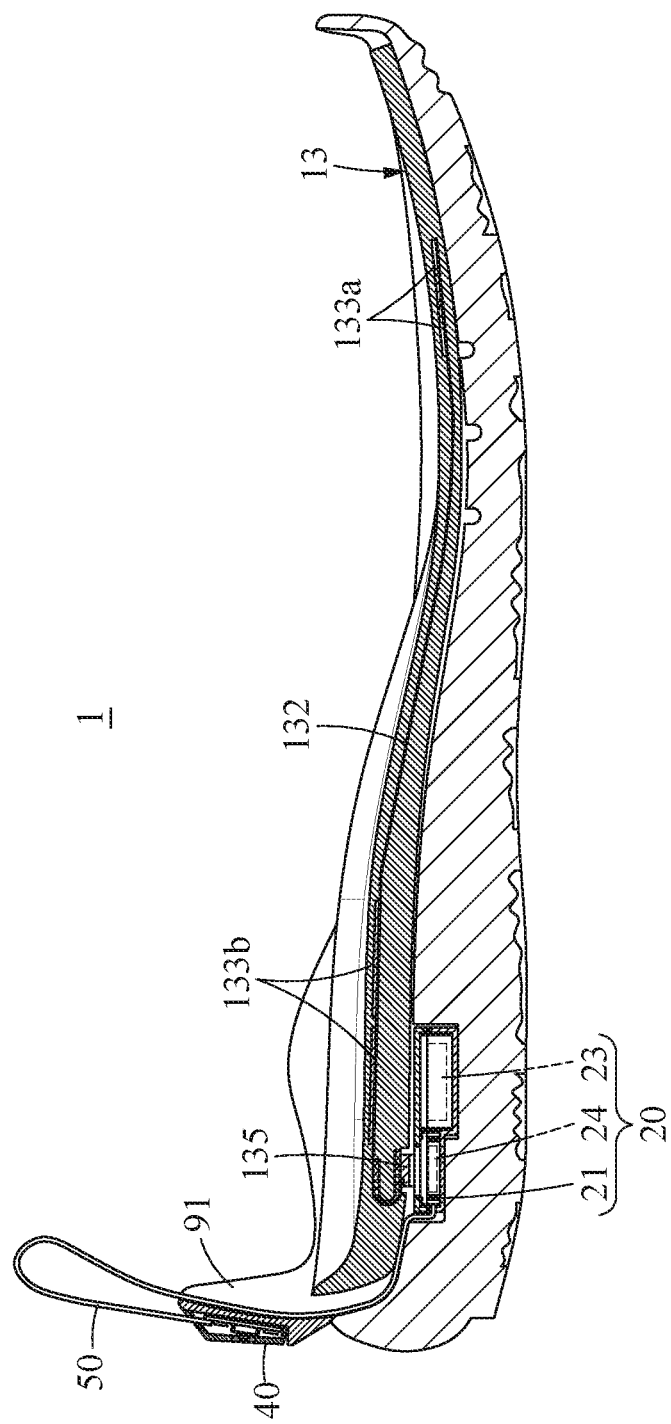
FIG. 3 is a cross-sectional view of a shoe according to at least one example embodiment.

FIG. 1 is a perspective view of a shoe according to at least one example embodiment, FIG. 2 is an exploded perspective view of a shoe and a partially cut insole body according to at least one example embodiment, and FIG. 3 is a cross-sectional view of a shoe according to at least one example embodiment.

Referring to FIGS. 1 through 3, a shoe 1 may include a sole 10, a control module (or, alternatively, a control device) 20, a user interface 40, an extension line 50, and an upper 90. The sole 10 may include an outsole 11, a midsole 12, and an insole 13.

The outsole 11 may form at least a portion of a bottom portion of the shoe 1. For example, the outsole 11 may include a bottom surface in contact with ground when the user wears the shoe 1 and may be formed using a robust material, for example, leather, rubber, and urethane, compared to that of the midsole 12. Although the following description is made based on an example in which the outsole 11 and the midsole 12 are distinguished from each other, the outsole 11 and the midsole 12 may be internally formed using the same material.

The midsole 12 may form at least a portion of a lower external appearance of the shoe 1. The midsole 12 may be provided on the outsole 11 and may include a receiving groove 121 that is recessed downward from a top surface of the midsole 12. The receiving groove 121 may be provided in a rear portion of the midsole 12 configured to support a heel of the user when the user wears the shoe 1. The rear portion of the midsole 12 may have a relatively thick thickness compared to those of other portions of the midsole 12. For example, since the midsole 12 becomes gradually thicker as getting closer to the rear portion, a front portion of the midsole 12 may have a thickness less than that of a portion of supporting the heel of the user. Compared to other portions, the rear portion of the midsole 12 may relatively easily secure an available space. When the user walks with wearing the shoe 1, a relatively great deformation may occur in a central portion of the midsole 12 that is an area between a portion of supporting a forefoot of the user and a portion of supporting the heel of the user.

The insole 13 includes a surface in contact with the sole of the user, and may be provided on the midsole 12 within the upper 90 to support the foot of the user. The insole 13 may be formed using a further flexible material than that of the midsole 12 and may enhance a sense of feeling when the user wears the shoe 1. For washing or replacement, the insole 13 may be separate from the midsole 12 and may be received after washing or replacing.

The insole 13 may include an insole body 131, a support layer 132, an electronic element 133, a connection line 134, and a connector 135.

The insole body 131 may be received on the top surface of the midsole 12. The insole body 131 may be manufactured in various shapes and formed of a flexible material. The insole body 131 may be manufactured to fit a sole shape of the user. For example, a width of a front portion of the insole body 131 may be greater than that of a rear portion thereof. When the insole 13 is received in the shoe 1, edge of the insole body 131 may be encompassed by the upper 90. The edge of the insole body 131 may protrude upward relative to the center of the insole body 131.

The support layer 132 may be provided in the insole body 131 and may support the electronic element 133 and the connection line 134. The support layer 132 may not be exposed to the outside with being encompassed by the insole body 131. The support layer 132 may be provided as a film of a flexible material.

Also, the electronic element 133 may be provided in the insole body 131. For example, the electronic element 133 may be provided on a top surface of the support layer 132 that faces the sole of the user, and the entire electronic element 133 and the support layer 132 may be provided in the insole body 131. Although four electronic elements 133 are illustrated, it is provided as an example only. One or more electronic elements 133 may be present. The electronic element 133 may deliver stimuli to the foot of the user, may measure a pressure applied from the foot of the user, and/or may sense a motion of the foot of the user. For example, the electronic element 133 may include at least one of a vibrator, a pressure sensor, and an inertial sensor.

The electronic element 133 may include the vibrator, for example, an eccentric motor. The eccentric motor may cause stochastic resonance on the sole of the user. For example, the electronic element 133 may generate vibration noise of a tactile threshold sensible by the sole of the user and may provide the vibration noise to the sole of the user. In this case, a tactile signal transferred to the sole of the user is amplified by resonance with the vibration noise and a sense of the sole of the user may become acute.

The electronic element 133 may include the pressure sensor, for example, a piezo pressure sensor or a force sensitive resistor (FSR) pressure sensor. The pressure sensor may measure a magnitude of pressure applied from the sole of the user. The measured information may be used to analyze a gait posture of the user.

The electronic element 133 may include the inertial sensor. The inertial sensor may measure acceleration, a speed, and a direction of each portion, for example, a front portion or a rear portion, of the foot of the user. The measured information may be used to analyze a gait pattern of the user.

The electronic elements 133 may include a front electronic element 133a and a rear electronic element 133b. Based on a state in which the user wears the shoe 1, the front electronic element 133a may face a front portion of the foot of the user and the rear electronic element 133b may face the heel of the foot of the user. An example of an arrangement structure of the electronic element 133 is further described with reference to FIG. 9.

The connection line 134 may electrically be connected to the electronic element 133 and the connector 135. One end of the connection line 134 may be connected to the electronic element 133 and another end thereof may be connected to the connector 135.

The connector 135 may electrically connect the electronic element 133 to the control module 20. The connector 135 may be connected to the connection line 134 and the connection line 134 may be connected to the electronic element 133. Once the connector 135 accesses the control module 20, the electronic element 133 and the control module 20 may be electrically connected. The connector 135 that serves to make the connection line 134 access the control module 20 may be provided in, for example, the rear portion of the insole 13 and enables physical contact between the connection line 134 and the control module 20. The connector 135 is detachably provided to the control module 20. The electronic element 133 and the control module 20 may be electrically connected when the connector 135 is attached to the control module 20, and may be electrically disconnected when the connector 135 is detached from the control module 20. The connector 135 may include a base 1351 fixed to support layer 132 and a detachable member 1352 detachable relative to the control module 20.

The control module 20 may electrically be connected to the electronic element 133 and may control an operation of the electronic element 133. For example, when the electronic element 133 includes a vibrator, the control module 20 may control a number of vibrations and/or an amplitude of the electronic element 133. The control module 20 may receive information from the electronic element 133. For example, when the electronic element 133 includes a pressure sensor or an inertial sensor, the control module 20 may receive information sensed at the electronic element 133. Although description is made based on an example in which the control module 20 communicates with the electronic element 133 through physical contact with the connector 135, it is provided as an example only. The connector 135 may be omitted and the control module 20 may communicate with the electronic element 133 in a wireless manner.

The control module 20 may be provided to the midsole 12. For example, the control module 20 may be mounted to the receiving groove 121 formed in the rear portion of the midsole 12. The rear portion of the midsole 12 is relatively thicker compared to the front portion of the midsole 12 and is easy to secure an available space. Thus, the receiving groove 121 formed in the rear portion may stably receive the control module 20. Although a sudden load is applied to the front portion of the midsole 12 during a toe-off motion or a step-up motion of the user, a relatively uniform load is applied to the rear portion of the midsole 12 during an entire stance phase of the user and the rear portion of the midsole 12 has a relatively excellent buffering effect. Thus, a probability of damage to the control module 20 may be relatively low. Also, during a process between a heel-off motion and a toe-off motion of the user, a relatively high deformation may occur in the central portion of the midsole 12. A relatively uniform deformation may occur in the rear portion of the midsole 12. Thus, a probability of damage to the control module 20 may be relatively low.

The control module 20 may include a case 21, an access portion 22, a battery 23, and a processor 24.

The case 21 may be in a shape corresponding to a shape of the receiving groove 121. The case 21 may include a case body 211 and a fastening groove 212 recessed from the case body 211. A size and a shape of the receiving groove 121 may be provided to receive the entire control module 20. For example, a height of the receiving groove 121 may be greater than or equal to a thickness of the control module 20 to inhibit (or, alternatively, prevent) the top surface of the control module 20 from protruding from the top surface of the midsole 12 when the control module 20 is received in the receiving groove 121.

The fastening groove 212 is configured to engage with the detachable member 1352, and thus may inhibit (or, alternatively, prevent) the connector 135 from deviating from above the case 21. For example, the fastening groove 212 may be provided to the left and/or the right of the case body 211 and a protrusion formed in the detachable member 1352 may couple with the fastening groove 212. A location of the fastening groove 212 is not limited thereto. Through the above fastening structure, a short-circuit issue between the connector 135 and the control module 20 may be avoided (or, alternatively, prevented) from occurring during various foot motions of the user.

The access portion 22 includes a terminal configured to be electrically contactable with the connection line 134. The access portion 22 may be provided on the case 21 and may make a contact with a terminal of the connection line 134. For example, in response to coupling between the connector 135 and the control module 20, the terminal of the access portion 22 may be electrically connected through contact with the terminal of the connection line 134.

The battery 23 may supply power to the electronic element 133 and the processor 24. The battery 23 may be received in the case 21.

The processor 24 may control the electronic element 133. The processor 24 may be received in the case 21.

For example, the control module 10 may include a memory and the processor 24, where the memory contain instructions that, when executed by the processor 24, configure the processor 24 as a special purpose processor to control the electronic element 133. For example, when the electronic element 133 includes a vibrator, the processor 24 may amplify a level of a signal that is too low for a user to sense by adding white noise, which has a wide frequency range, to the signal to cause a portion of the white noise having the same frequency as the signal to resonate with the signal thus amplifying the signal and allowing the user to sense the signal. In one or more example embodiments, the control module 20 is incorporated in the receiving groove 121 in the midsole 12, the user interface 40 is secured to an outside of the shoe 1, and the connector 135 includes a detachable member 1352 that allows the insole 13 to be detachably connected to the control module 20, and as such, battery capacity and user convenience may be increased.

The user interface 40 may couple with a rear portion of the upper 90. The user interface 40 may receive a user instruction for controlling the electronic element 133. For example, user instruction may include a power instruction for powering ON or OFF the electronic element 133. The user interface 40 is attachable to or detachable from a back counter 91 of the upper 90, the back counter 91 may be a portion of the upper 90 of the shoe that forms the back of the shoe and connects to the heel. For example, the user interface 40 may tightly fit the back counter 91 or may slide relative to the back counter 91 in a height direction of the back counter 91. The back counter 91 may be formed using a relatively robust material compared to that of an upper body 92. In this case, it is possible to reduce interference with an attachable/detachable operation of the user interface 40 by deformation of the upper 90. Since the user interface 40 is placed at an outside of the shoe 1 to be separate from the control module 20, the control module 20 provided to the midsole 12 may be manufactured to have a further reduced size.

The extension line 50 may connect the control module 20 and the user interface 40 for access. For example, the extension line 50 may be provided to surround the back counter 91 in the height direction of the back counter 91. According to the above structure, the user may use the extension line 50 to hold the shoe 1. At least a portion of the extension line 50, for example, a portion that is not exposed to the outside of the shoe 1 is fastened within the back counter 91. A portion of the remaining, for example, a portion adjacent to the user interface 40 that is exposed to the outside of the shoe 1 may not be fastened to the back counter 91. According to the above structure, the user may separate the user interface 40 from the back counter 91 by pulling the extension line 50. The extension line 50 may be formed using a fabric material and a width of the extension line 50 may be relatively wider than a thickness of the extension line 50.

The control module 20, the extension line 50, and the user interface 40 may be referred to as a control assembly.

The upper 90 may form an upper external appearance of the shoe 1 and may wrap around the foot of the user. A lower end edge of the upper 90 may be connected to the midsole 12, and may include the back counter 91 configured to support a vertical portion of the heel of the user. Hereinafter, for clarity of description, a portion excluding the back counter 91 from the upper 90 is referred to as the upper body 92.

The back counter 91 may wrap around a rear edge of the midsole 12 and may extend upward from the midsole 12. The back counter 91 may be formed using a relatively robust material compared to that of the upper body 92 and may support the upper body 92 to maintain its external appearance. For example, an inner side of the back counter 91 may be fastened at the rear of the upper body 92 and may support the upper body 92. The extension line 50 may be provided on an inner surface of the back counter 91. The upper body 92 may be formed with the extension line 50 being placed on the inner surface of the back counter 91. Accordingly, the extension line 50 may be provided between the back counter 91 and the upper body 92.

Figure 4:
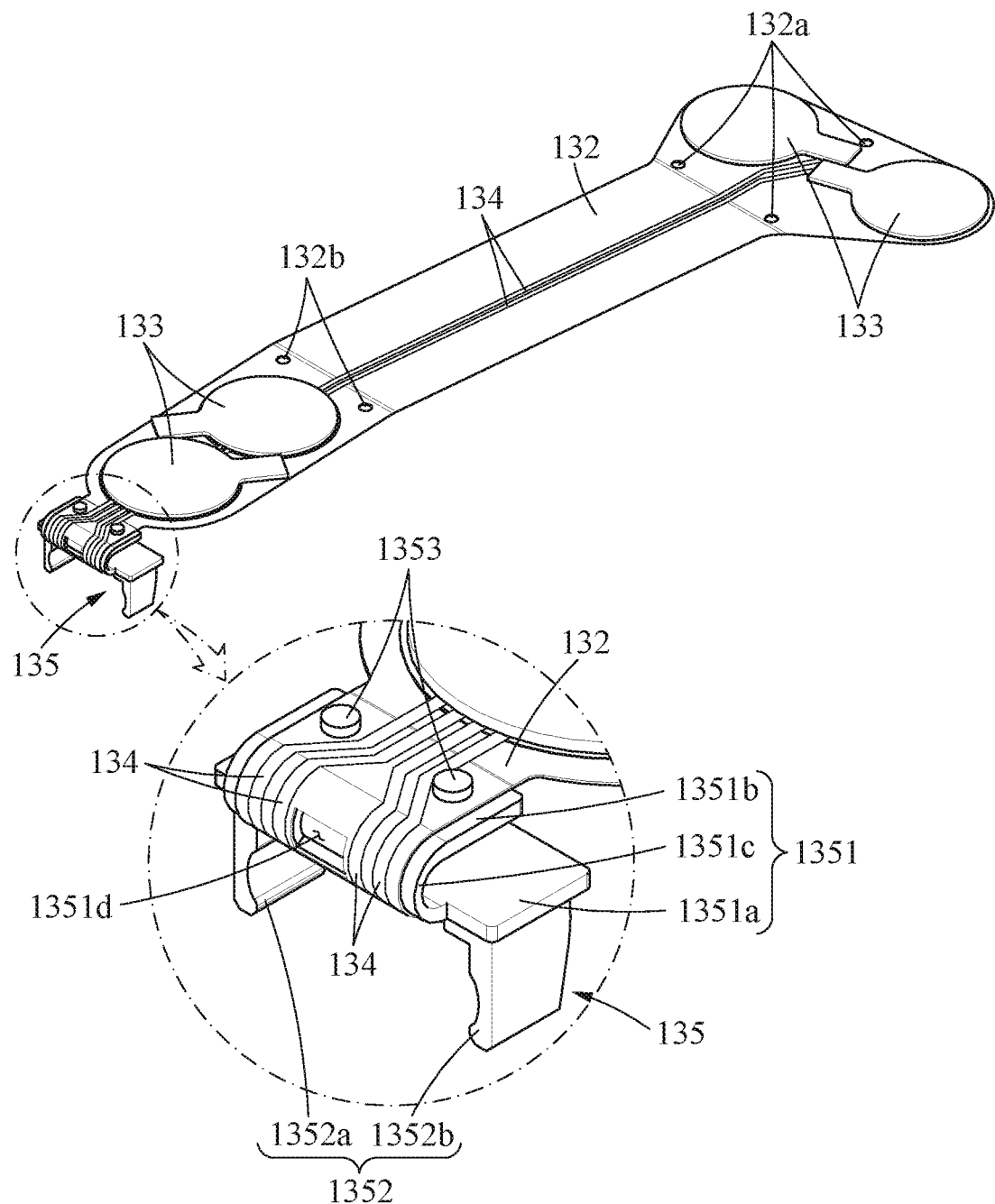
FIG. 4 is a perspective view and a partially enlarged perspective view illustrating components embedded in an insole body according to at least one example embodiment.
Figure 5:
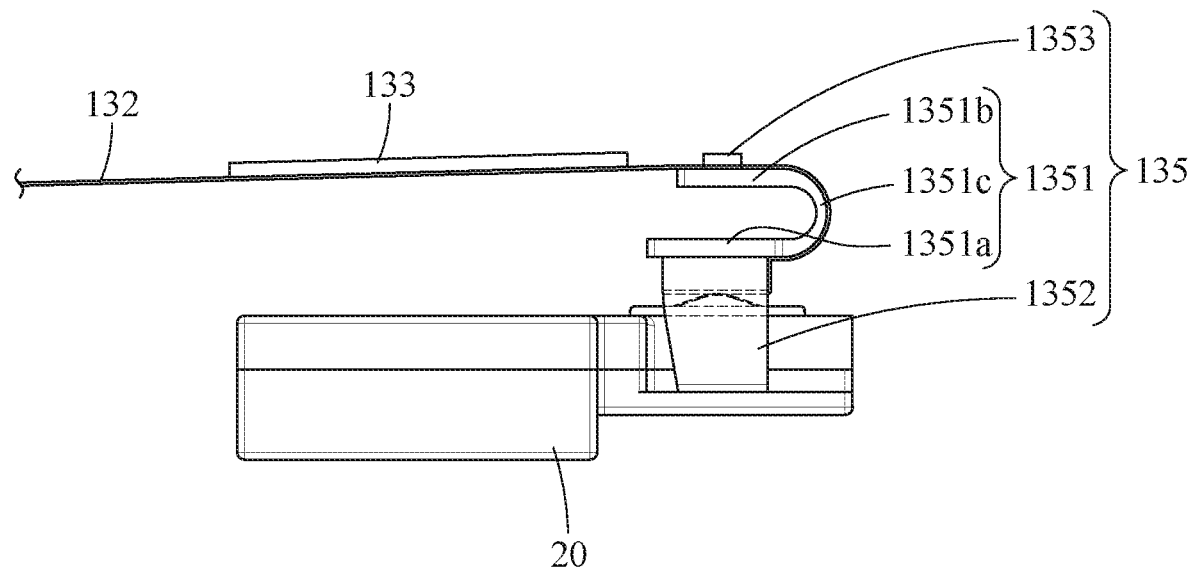
FIG. 5 is a side view illustrating an example in which a connector couples with a control module according to at least one example embodiment.
Figure 6:
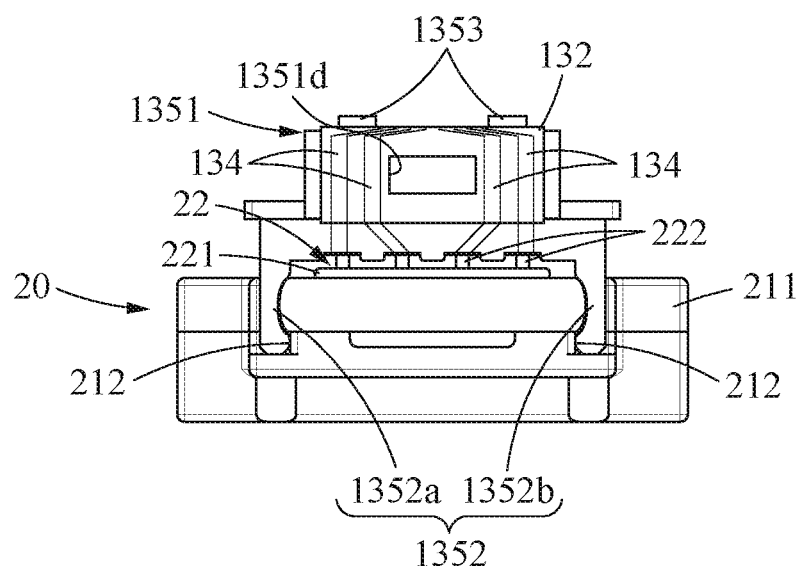
FIG. 6 is a rear view illustrating an example in which a connector couples with a control module according to at least one example embodiment.
Figure 7:
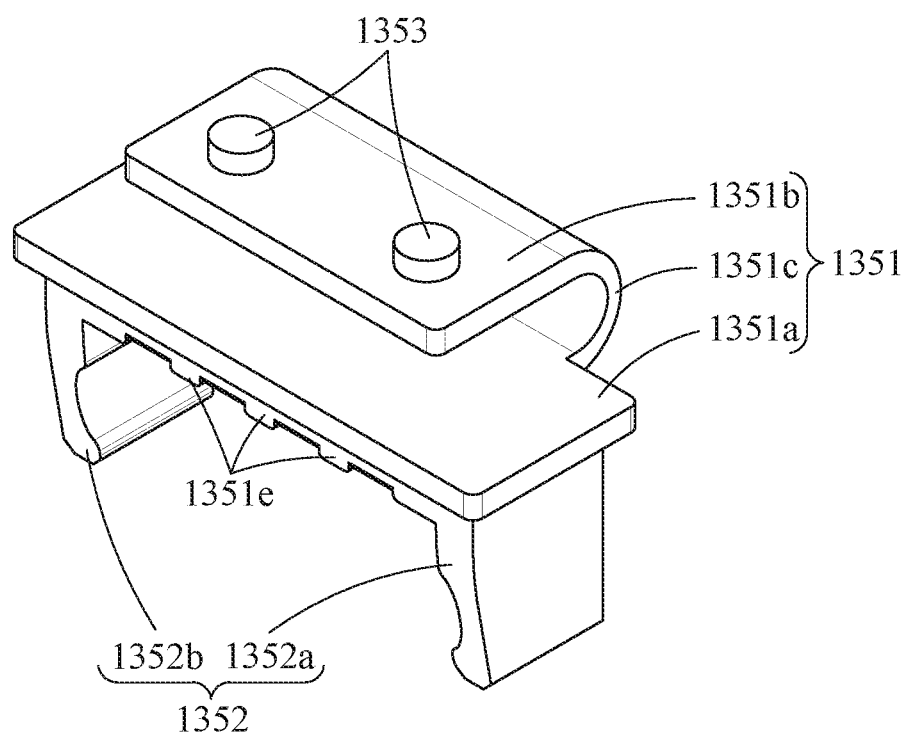
FIG. 7 is a perspective view of a connector according to at least one example embodiment.
Figure 8:
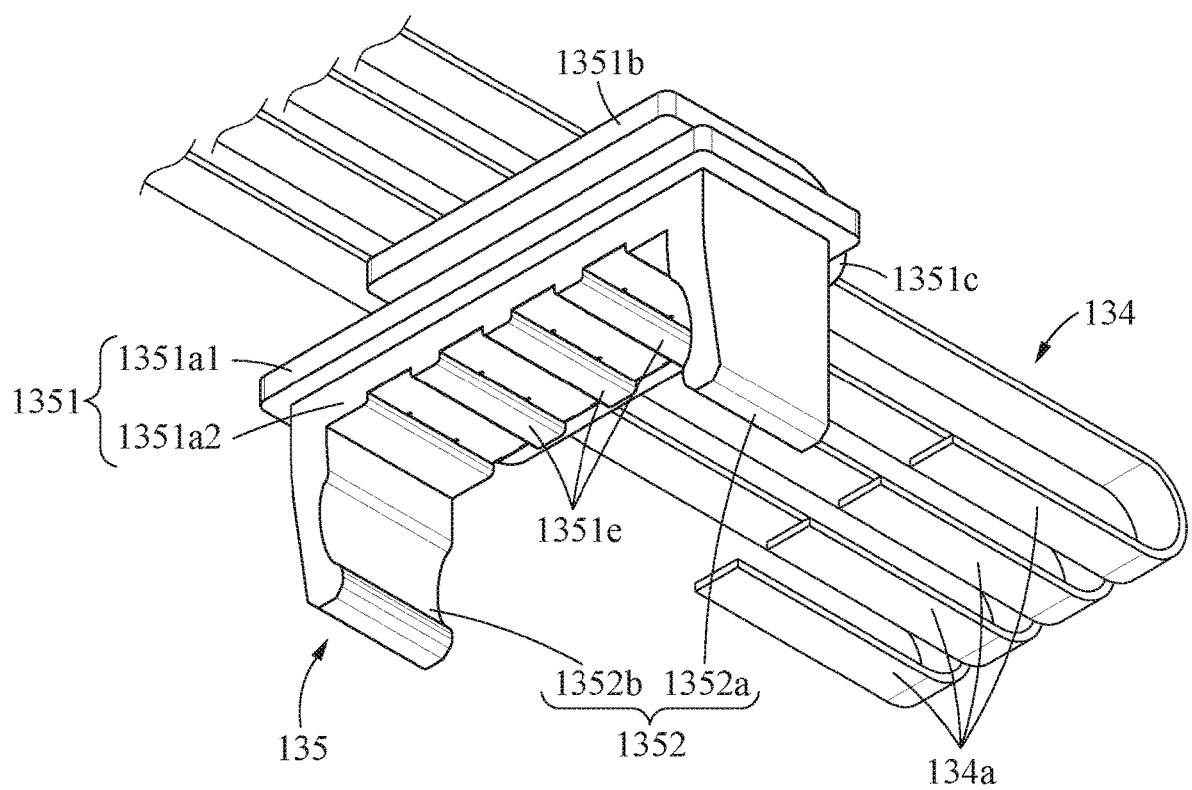
FIG. 8 is a perspective view of a connector viewed at another angle according to at least one example embodiment.

FIG. 4 is a perspective view and a partially enlarged perspective view illustrating components embedded in an insole body according to at least one example embodiment, FIG. 5 is a side view illustrating an example in which a connector couples with a control module according to at least one example embodiment, FIG. 6 is a rear view illustrating an example in which a connector couples with a control module according to at least one example embodiment, FIG. 7 is a perspective view of a connector according to at least one example embodiment, and FIG. 8 is a perspective view of a connector viewed at another angle according to at least one example embodiment.

Referring to FIGS. 4 through 8, the support layer 132 that supports the plurality of electronic elements 133 may be fastened to the connector 135. For example, a rear end of the support layer 132 corresponding to the heel of the sole may wrap around the connector 135.

The connector 135 may be detachably provided to the control module 20. When the connector 135 is mounted to the control module 20, the connection line 134 may access the control module 20. The connector 135 may include the base 1351, the detachable member 1352, and a support protrusion 1353.

The base 1351 may connect at an end that extends from the rear portion of the support layer 132. The base 1351 may downwardly expose each connection line 134 and may absorb an impact that is transferred to the control module 20. For example, the base 1351 may have elasticity and may be provided between the heel of the user wearing the shoe 1 and the control module 20. While the user is walking, the base 1351 may absorb at least a portion of impact vertically transferred due to the weight of the user, thereby decreasing an amount of impact transferred to the control module 20.

The base 1351 may include a lower plate 1351a, an upper plate 1351b, a connection member 1351c, a fluid through hole 1351d, and a plurality of ribs 1351e.

Referring to FIG. 8, the connection line 134 may wrap around the base 1351. A contact terminal 134a that is one end of the connection line 134 may be attached on a bottom surface of the base 1351 and exposed to the outside.

The lower plate 1351a may downwardly expose the connection line 134. For example, the connection line 134 may wrap around the base 1351 and the connection line 134 may be downwardly exposed. The lower plate 1351a may include a main lower plate 1351a1 and an auxiliary lower plate 1351a2. A size of the main lower plate 1351a1 may be greater than that of the auxiliary lower plate 1351a2. The auxiliary lower plate 1351a2 may be provided at a center portion of the main lower plate 1351a1. A step may be formed between the main lower plate 1351a1 and the auxiliary lower plate 1351a2. For example, edge of the main lower plate 1351a1 may not overlap the auxiliary lower plate 1351a2 when viewed from up to down in a vertical direction.

The upper plate 1351b may be separate from the lower plate 1351a and may support the support layer 132. For example, a contact state between a top surface of the upper plate 1351b and a bottom surface of the support layer 132 may be maintained.

The connection member 1351c may connect the lower plate 1351a and the upper plate 1351b. In response to an impact applied to the base 1351, the connection member 1351c may be deformed. For example, a convex portion of the connection member 1351c may be in a U shape toward the rear of the insole body 131 (see FIG. 2). During a heel strike motion of the user, the upper plate 1351b may be pressed downward and a distance between the lower plate 1351a and the upper plate 1351b may be reduced. During a heel-off motion of the user, the upper plate 1351b may return to an original state. Through the above structure, the base 1351 may absorb a portion of impact occurring due to the foot of the user while maintaining a state in which the connection line 134 is in contact with the control module 20 in a vertical direction relative thereto.

The fluid through hole 1351d may be formed in the connection member 1351c and may penetrate the connection member 1351c in a lengthwise direction of the support layer 132. During a manufacturing process, the fluid through hole 1351d may assist a foam material of the insole body 131 to be smoothly foamed. For example, the foam material may pass through the fluid through hole 1351d and may be smoothly foamed at the rear of the connection member 1351c. Also, the fluid through hole 1351d may assist the connection member 1351c to be further flexibly deformed. The support layer 132 may include a hole corresponding to the fluid through hole 1351d. The plurality of connection lines 134 may extend to the bottom surface of the lower plate 1351a by detouring the fluid through hole 1351d.

The plurality of ribs 1351e may protrude downward from the lower plate 1351a. Each of the plurality of connection lines 134 may be provided on a surface on which the rib 1351c is absent, that is, on a recessed portion, on the bottom surface of the lower plate 1351a. Each rib 1351e may be provided between two adjacent connection lines 134. Likewise, the connection line 134 may be provided between two adjacent ribs 1351e. The rib 1351e may support a side portion of the connection line 134 and may assist alignment of the connection line 134. Also, the terminal of the access portion 22 included in the control module 20 may insert between the ribs 1351e and may be in contact with the terminal of the connection line 134, thereby securing a connection state between the terminal of the access portion 22 and the terminal of the connection line 134. For example, the contact terminal 134a of the connection line 134 may be provided between two adjacent ribs 1351e.

The detachable member 1352 may be detachably provided to the control module 20. For example, at least a portion of the detachable member 1352 may insert into the fastening groove 212 that is provided to the case 21 of the control module 20. A portion of the detachable member 1352 may protrude from the bottom surface of the insole body 131 to enable insertion. As a protruding structure, the detachable member 1352 may include a left arm 1352a and a right arm 1352b.

The left arm 1352a protrudes downward from the left side of the base 1351a and couples with the left side of the control module 20. For example, an inner side portion of the left arm 1352a may wrap around a left-side surface of the control module 20, and an end of the left arm 1352a may insert into the fastening groove 212 that is recessed from a left-side surface of the case body 211.

Likewise, the right arm 1352b protrudes downward from the right side of the base 1351a and couples with the right side of the control module 20. For example, an inner side portion of the right arm 1352b may wrap around a right-side surface of the control module 20, and an end of the right arm 1352b may insert into the fastening groove 212 that is recessed from a right-side surface of the case body 211. The right arm 1352b and the left arm 1352a may be provided to face each other in a corresponding shape.

In general, during dorsiflexion and/or planar flexion of the user, lateral deformation of the insole body 131 (see FIG. 2) is relatively small compared to forward and backward deformation of the insole body 131. Accordingly, the left arm 1352a and the right arm 1352b may stably maintain a fastening state with the control module 20 while the user is walking.

As another example, the detachable member 1352 may be in a structure of a hook-and-loop fastener or a snap fit.

The support protrusion 1353 may protrude upward from the base 1351. An opening through which the support protrusion 1353 may pass may be included in the support layer 132. Once the support protrusion 1353 passes through and thereby couples with the opening, the support protrusion 1353 may further secure fastening between the base 1351 and the support layer 132, thereby inhibiting (or, alternatively, preventing) the support layer 132 from moving relative to the base 1351. Two or more support protrusions 1353 may be provided.

Figure 9:
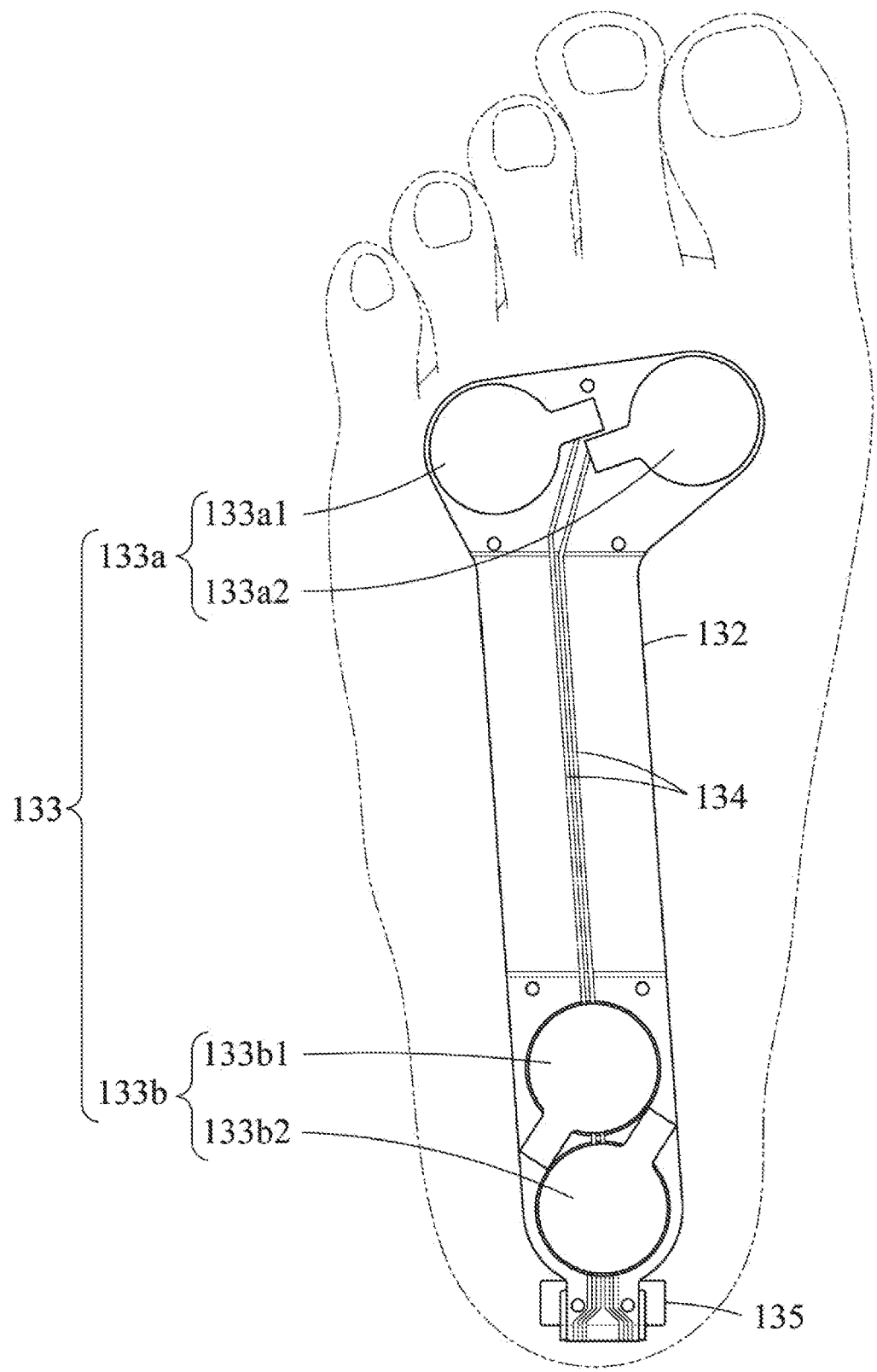
FIG. 9 is a top view illustrating an example of a relative positional relationship between an electronic element and a foot of a user according to at least one example embodiment.

FIG. 9 is a top view illustrating an example of a relative positional relationship between an electronic element and a foot of a user according to at least one example embodiment.

Referring to FIG. 9, the plurality of electronic elements 133 may include the front electronic element 133a provided in a front portion of the support layer 132 and the rear electronic element 133b provided in a rear portion of the support layer 132.

The front electronic element 133a may include a first front electronic element 133a1 and a second front electronic element 133a2 that are arranged in a widthwise direction of the support layer 132. The first front electronic element 133a1 may be arranged at a location relatively adjacent to a little toe of the user in the support layer 132. The second front electronic element 133a2 may be arranged at a location relatively adjacent to a big toe of the user in the support layer 132. When each of the first front electronic element 133a 1 and the second front electronic element 133a2 includes a vibrator, the first front electronic element 133a1 may apply stimuli to an outer side portion in a front portion of the sole of the user and the second front electronic element 133a2 may apply stimuli to an inner side portion in the front portion of the sole of the user. When each of the first front electronic element 133a1 and the second front electronic element 133a2 includes a sensor, the first front electronic element 133a1 and the second front electronic element 133a2 may sense inversion and/or eversion of the user. For example, when the inversion occurs in the ankle of the user, the first front electronic element 133a1 may sense pressure and the second front electronic element 133a2 may not sense the pressure. When the eversion occurs in the ankle of the user, the first front electronic element 133a1 may not sense the pressure and the second front electronic element 133a2 may sense the pressure.

The rear electronic element 133b may include a first rear electronic element 133b1 and a second rear electronic element 133b2 that are arranged in a lengthwise direction of the support layer 132. The first rear electronic element 133b1 may be provided relatively forward of the heel of the user and the second rear electronic element 133b2 may be provided relatively rearward of the heel of the user. When each of the first rear electronic element 133b1 and the second rear electronic element 133b2 includes a sensor, the first rear electronic element 133b1 and the second rear electronic element 133b2 may further precisely sense a gait state of the user. For example, during the progress of heel strike, the first rear electronic element 133b1 may not sense pressure and the second rear electronic element 133b2 may sense the pressure. During the progress of mid-stance, all of the first rear electronic element 133b1 and the second rear electronic element 133b2 may sense the pressure.

Figure 10:
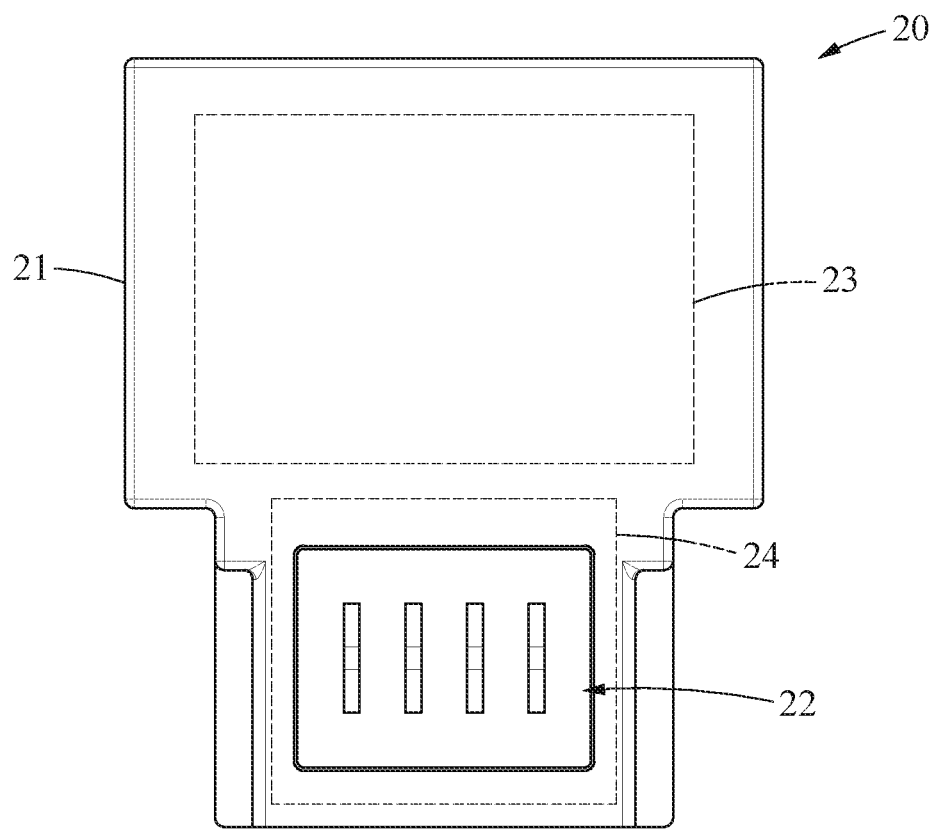
FIG. 10 is a top view of a control module according to at least one example embodiment.
Figure 11:
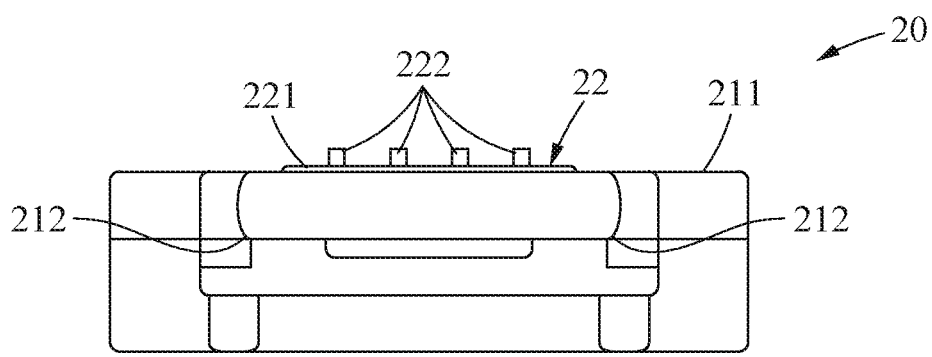
FIG. 11 is a rear view of a control module according to at least one example embodiment.
Figure 12:
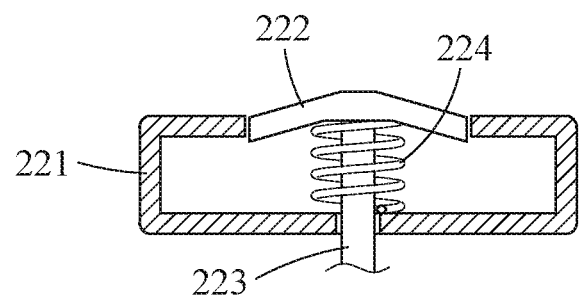
FIG. 12 is a cross-sectional view of an access portion according to at least one example embodiment.
Figure 13:
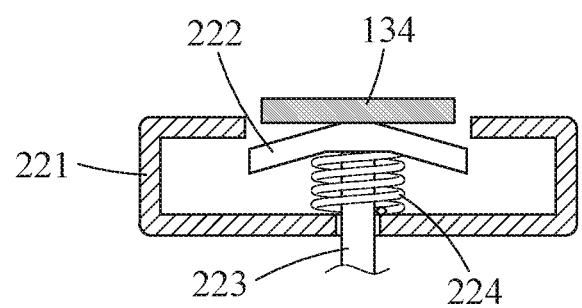
FIG. 13 is a cross-sectional view of an access portion and illustrates a state in which an access terminal and a connection line are in contact according to at least one example embodiment.

FIG. 10 is a top view of a control module according to at least one example embodiment, FIG. 11 is a rear view of a control module according to at least one example embodiment, FIG. 12 is a cross-sectional view of an access portion according to at least one example embodiment, and FIG. 13 is a cross-sectional view of an access portion and illustrates a state in which an access terminal and a connection line are in contact according to at least one example embodiment.

Referring to FIGS. 10 to 13, the control module 20 may include the case 21, the access portion 22, the battery 23, and the processor 24. The case 21 may include the case body 211 and the fastening groove 212. The access portion 22 may include an access body 221, an access terminal 222, an access line 223, and an elastic member 224.

The access body 221 may be provided on the case 21. The access body 221 may have a space in which the access terminal 222 may move vertically.

The access terminal 222 may access the contact terminal 134a (see FIG. 8) of the connection line 134. For example, the access terminal 222 may vertically move, may be in physical contact with the contact terminal 134a of the connection line 134, and may electrically connect thereto. At least a portion of the access terminal 222 may be received in the access body 221 and may move vertically relative to the top surface of the case 21. The top surface of the access terminal 222 may be flat for easy contact with the connection line 134.

The access line 223 may extend from the bottom surface of the access terminal 222 and may electrically be connected to the battery 23 and/or the processor 24. The access terminal 222 and the battery 23 may be electrically connected through the connection line 50. In response to turning OFF a power button 43 (see FIG. 14) of the user interface 40, the access terminal 222 and the battery 23 may be electrically disconnected, which may lead to suspending the power supply to the electronic element 133.

The elastic member 224 may support the access terminal 222 to maintain a stable contact state with the connection line 134. For example, the elastic member 224 may be a linear spring or a rubber pad. The elastic member 224 may be received in the access body 221 such that an upper end of the elastic member 224 may be connected to the access terminal 222 and a lower end thereof may be fastened to the access body 221. In a state in which the connection line 134 is in contact with the access terminal 222, the elastic member 224 may be configured to press the access terminal 222 upward. Accordingly, a force of maintaining a contact point during a gait may be enhanced.

Figure 14:
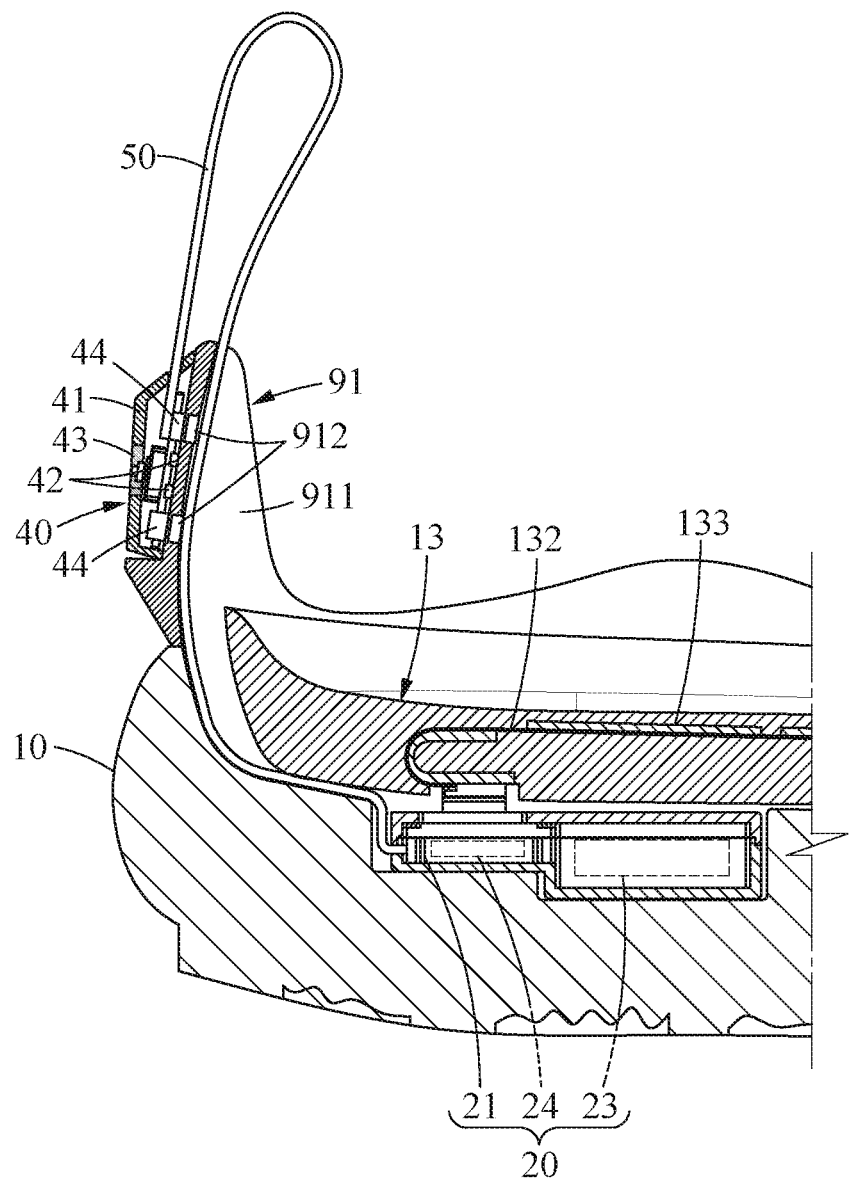
FIG. 14 is a cross-sectional view of a shoe according to at least one example embodiment.
Figure 15:
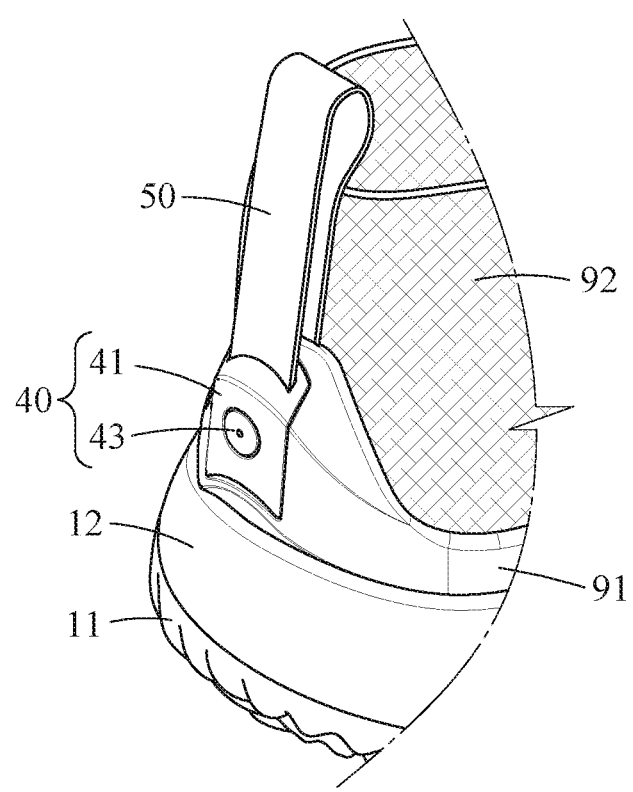
FIG. 15 is a partially enlarged perspective view of a shoe and illustrates a state in which a user interface is mounted to a back counter according to at least one example embodiment.
Figure 16:
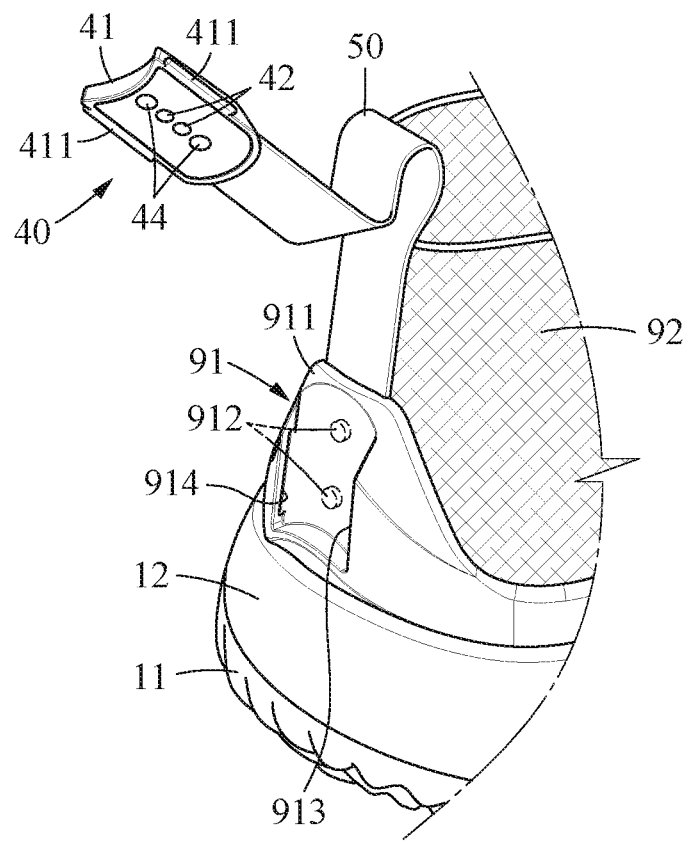
FIG. 16 is a partially enlarged perspective view of a shoe and illustrates a state in which a user interface is separate from a back counter according to at least one example embodiment.
Figure 17:
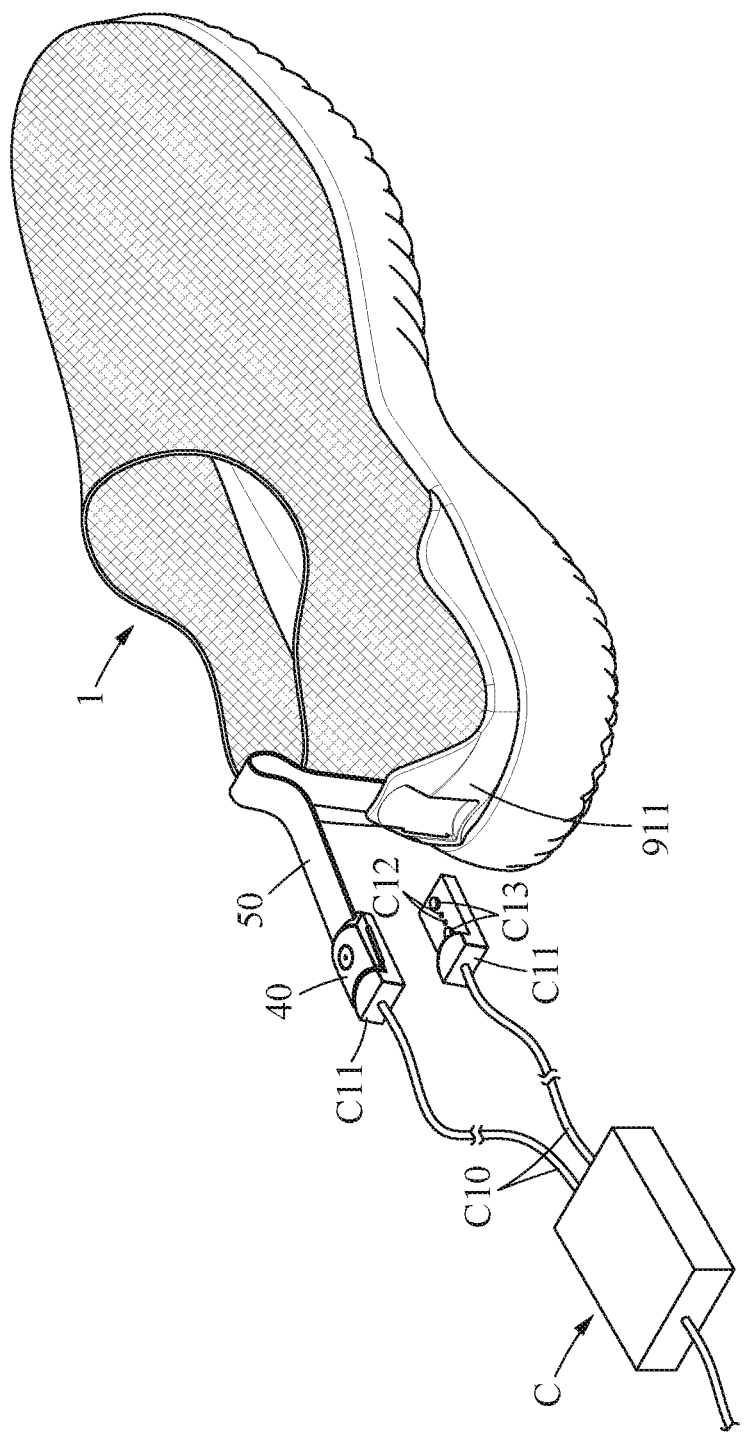
FIG. 17 is a perspective view illustrating a state in which a user interface couples with an external power supply device according to at least one example embodiment.

FIG. 14 is a cross-sectional view of a shoe according to at least one example embodiment, FIG. 15 is a partially enlarged perspective view of a shoe and illustrates a state in which a user interface is mounted to a back counter according to at least one example embodiment, FIG. 16 is a partially enlarged perspective view of a shoe and illustrates a state in which a user interface is separate from a back counter according to at least one example embodiment, and FIG. 17 is a perspective view illustrating a state in which a user interface couples with an external power supply device according to at least one example embodiment.

Referring to FIGS. 14 to 17, the user interface 40 may be detachably provided to an outer side of the back counter 91 of the upper 90. When the user interface 40 is attached to the upper 90, the user interface 40 may include an exposed surface that is exposed to the outside and a non-exposed surface that is not exposed to the outside.

The user interface 40 may include an interface body 41, a battery charging terminal 42, the power button 43, and an interface magnetic substance 44.

For example, the interface body 41 may couple with the back counter 91 using a tight fit scheme or a sliding scheme. The interface body 41 may include a connection protrusion 411 that protrudes from the left-side surface and/or the right-side surface of the interface body 41 and has elasticity. The connection protrusion 411 may insert into a connection groove 914 provided to the back counter 91 using the tight fit scheme or the sliding scheme, and may inhibit (or, alternatively, prevent) the coupled interface body 41 from being easily detached from the back counter 91 due to an external impact.

A mounting portion 913 provided to the back counter 91 may have the connection groove 914 for attachment and detachment of the interface body 41 using the tight fit scheme or the sliding scheme. A lateral depth of the mounting portion 913 may be equal or similar to a lateral height of the interface body 41. Thus, in a mounting state, the shoe 1 may have a smooth rear surface.

The battery charging terminal 42 may be disposed on the non-exposed surface of the user interface 40. The battery charging terminal 42 may be covered by an outer wall of the back counter 91.

The power button 43 may power ON or OFF the electronic element 133. The power button 43 may power ON or OFF the electronic element 133 by changing, for example, the electrical connection between the battery 23 and the access terminal 222. The power button 43 may be disposed on the exposed surface of the user interface 40 and may be turned ON/OFF in response to the user pushing the power button 43. A light source, for example, a light emitting diode (LED) bulb, may be provided to the power button 43, and may indicate an ON/OFF state of the electronic element 133. For example, the light source may emit light only when the electronic element 133 is in an ON state.

The interface magnetic substance 44 may be disposed on the non-exposed surface of the user interface 40 and may provide a magnetic force for coupling the user interface 40 with an external power supply device C. For example, the interface magnetic substance 44 may be provided in parallel with the battery charging terminal 42.

The external power device C may include a power line C10, a power support C11 configured to support the user interface 40, a power charging terminal C12 configured to access the battery charging terminal 42, and a power magnetic substance C13 configured to provide a magnetic force to the interface magnetic substance 44. Two power lines C10, two power supports C11, two power charging terminals C12, and two power magnetic substances C13 may be provided to charge batteries provided to a left shoe and a right shoe, respectively.

The back counter 91 may include a back counter body 911, an upper magnetic substance 912, the mounting portion 913, and the connection groove 914.

The back counter body 911 may wrap around the rear end of the midsole 12 and may protrude upward from the midsole 12. The back counter body 911 may be formed using a relatively robust material compared to that of the upper body 92 and may include the mounting portion 913 configured to stably receive the user interface 40.

The upper magnetic substance 912 may couple with the interface magnetic substance 44 using a magnetic force and may enhance a coupling force of the user interface 40. The upper magnetic substance 912 may be provided in the back counter body 911 to face the interface magnetic substance 44.

The mounting portion 913 may be recessed from the outer surface of the back counter body 911 and may receive the user interface 40. The mounting portion 913 is in, for example, an upwardly open shape so that the interface body 41 may slidably couple with or separate from the mounting portion 913. To assist slidable coupling or separation, the mounting portion 913 may have the connection groove 914 capable of receiving the connection protrusion 411. The connection groove 914 may be recessed from one surface of the back counter 91 that forms the mounting portion 913.

Figure 18:
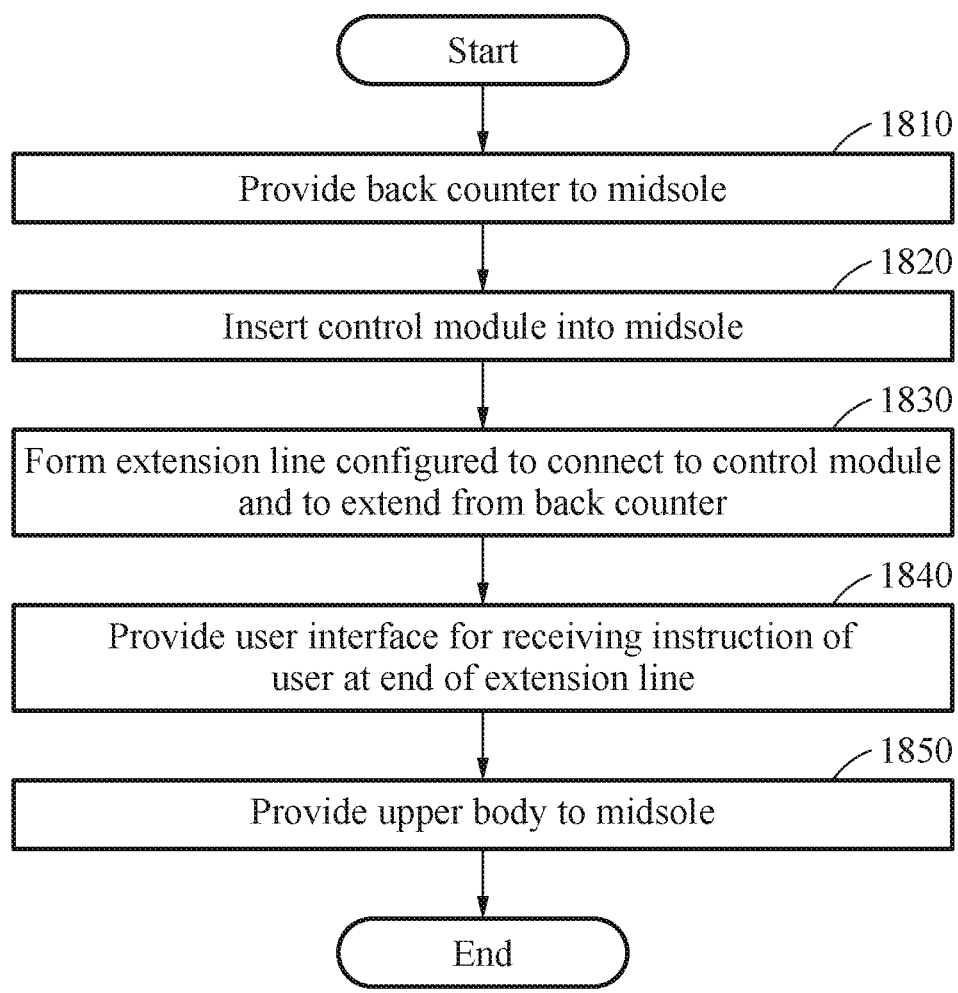
FIG. 18 is a flowchart illustrating a shoe manufacturing method according to at least one example embodiment.

FIG. 18 is a flowchart illustrating a shoe manufacturing method according to at least one example embodiment.

Referring to FIG. 18, the shoe manufacturing method may include operation 1810 of providing a back counter to a midsole, operation 1820 of inserting a control module into the midsole, operation 1830 of forming an extension line configured to connect to the control module and to extend from the back counter, operation 1840 of providing a user interface for receiving an instruction of a user at an end of the extension line, and operation 1850 of providing an upper body to the midsole. Order of each operation is provided as an example only and is not particularly limited unless defined otherwise.

In operation 1810, the back counter 91 may be provided to the midsole 12. For example, the back counter 91 may be connected to the midsole 12 to protrude upward from the rear of the midsole 12. The back counter 91 may be formed using a relatively robust material compared to that of the midsole 12.

In operation 1820, the control module 20 may be inserted into the midsole 12. For example, the midsole 12 may include the receiving groove 121 configured to receive the control module 20. The receiving groove 121 may be formed in a rear portion of the midsole 12. Here, the rear portion may refer to a portion for supporting a heel of a sole of the user.

In operation 1830, an extension line 50 may be formed in the control module 20. Operation 1830 may be performed prior to operations 1810 and/or 1820. The extension line 50 may extend along the back counter 91. For example, the extension line 50 may extend along an inner wall of the back counter 91.

In operation 1840, the user interface 40 may be provided at an end of the extension line 50. Operation 1830 may be performed prior to at least one of operations 1810, 1820, and 1830.

In operation 1850, the upper body 92 may be provided to the midsole 12. Operation 1850 may be performed after operations 1810, 1820, and 1830. That is, in a state in which the control module 20 is received in the midsole 12 and the extension line 50 is configured to extend along the inner wall of the back counter 91, the upper body 92 may be provided to the midsole 12. According to the shoe manufacturing method, since the extension line 50 is provided between an inner wall of the midsole 12 and an outer wall of the upper body 91, thereby enhancing fastening stability. Also, it is possible to diminish (or, alternatively, prevent) the extension line from interfering with a foot of the user.

Figure 19:
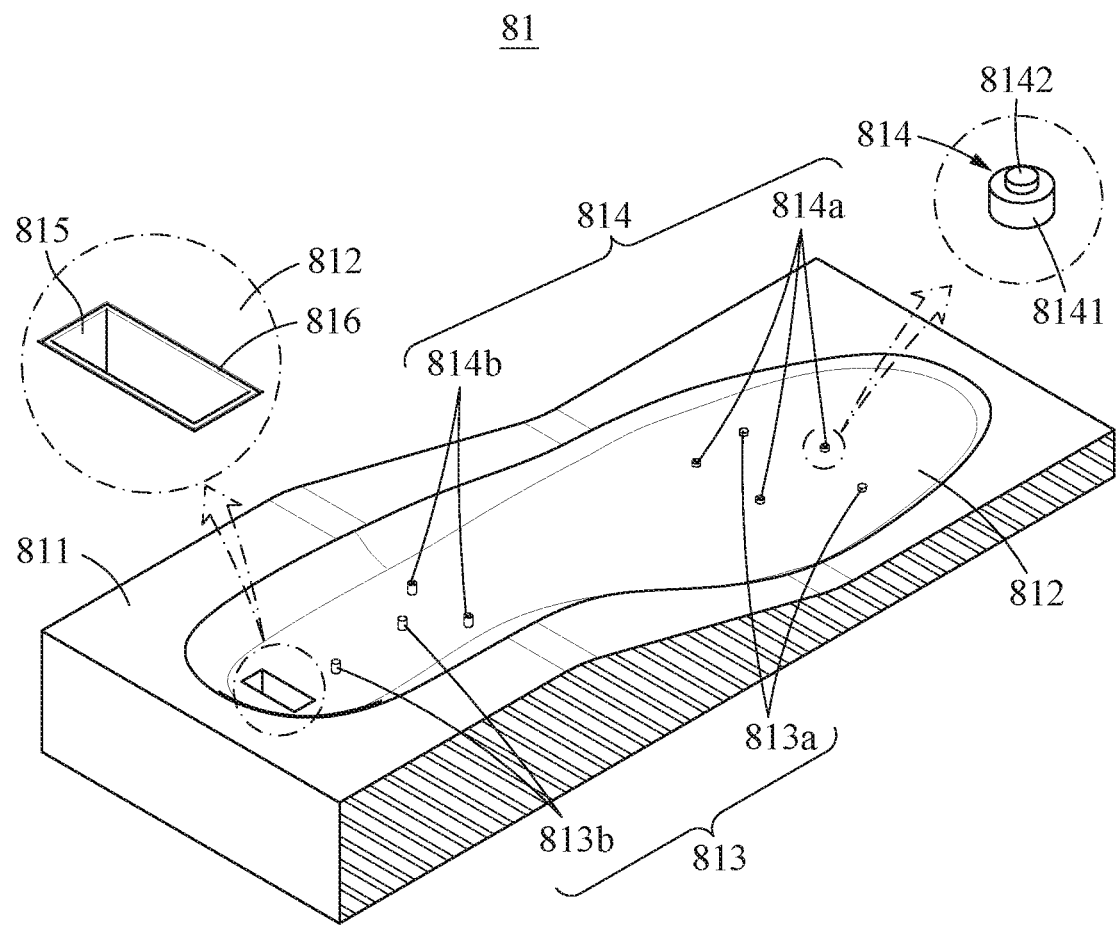
FIG. 19 is a perspective view illustrating a lower mold frame for manufacturing an insole according to at least one example embodiment.
Figure 20:
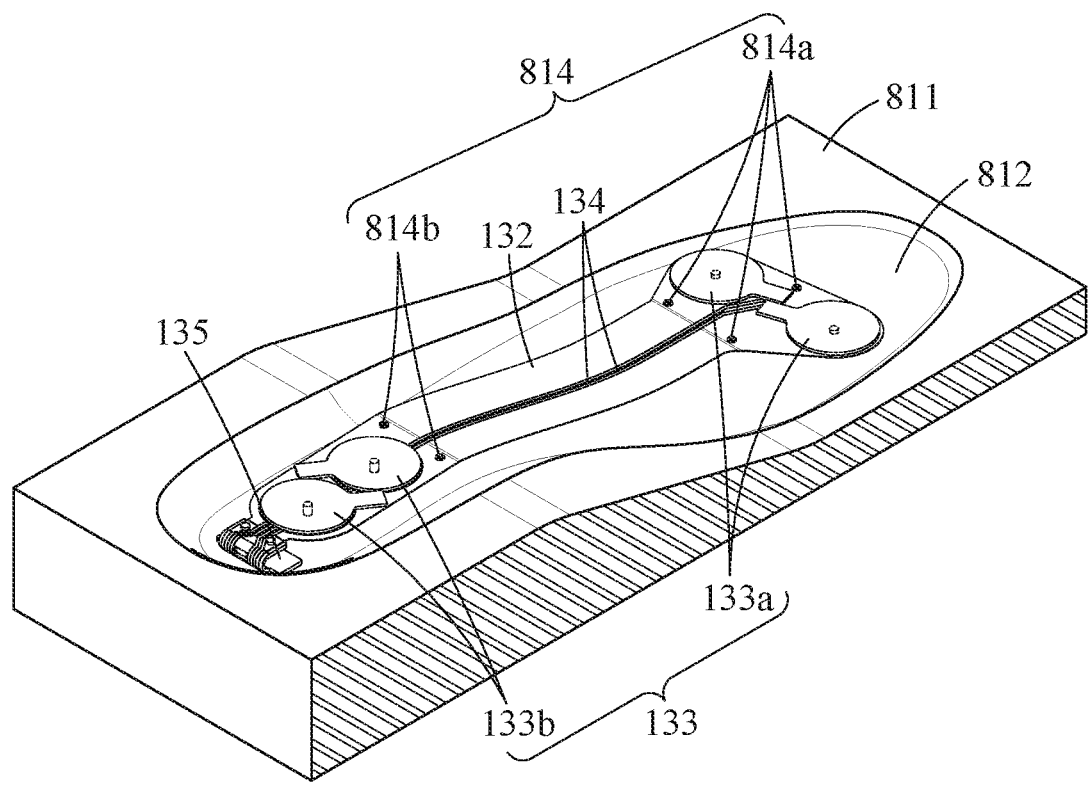
FIG. 20 is a perspective view illustrating a state in which a support layer is provided to a lower mold frame according to at least one example embodiment.
Figure 21:
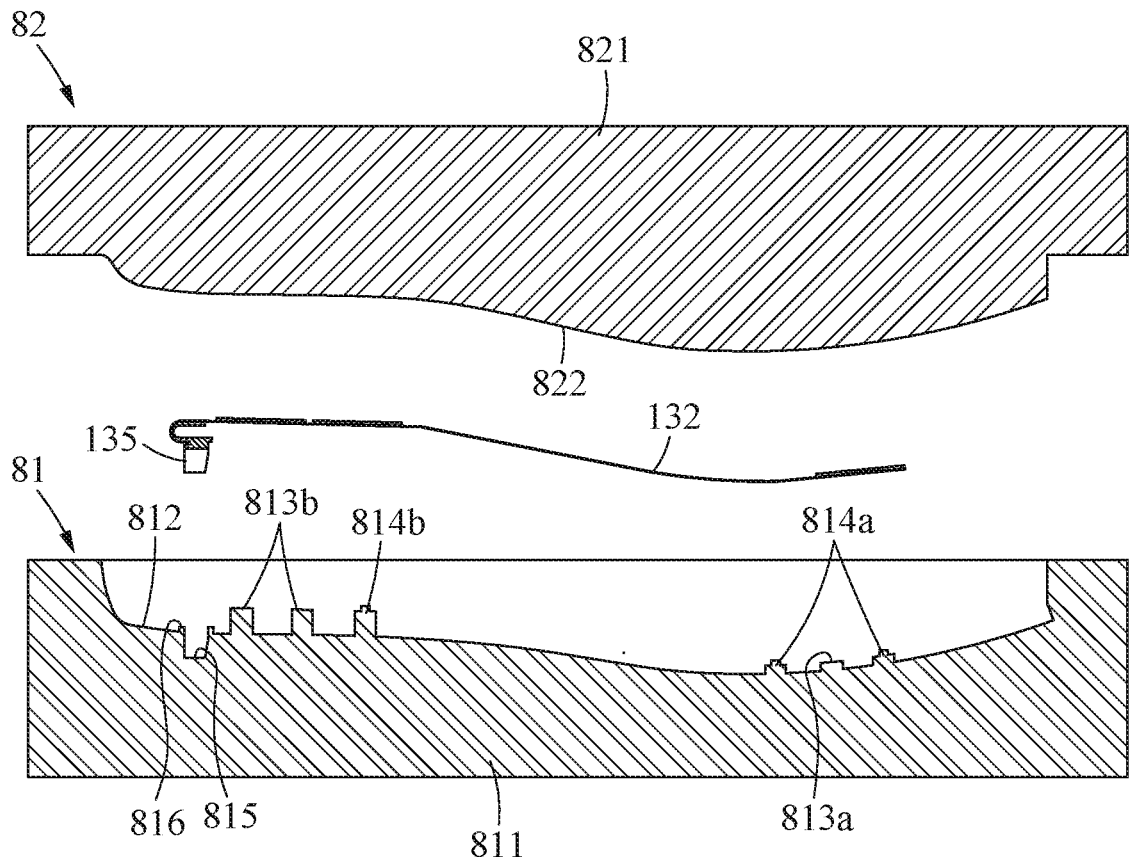
FIG. 21 is a cross-sectional view illustrating a state in which a lower mold frame, a support layer, and an upper mold frame are separate according to at least one example embodiment.
Figure 22:
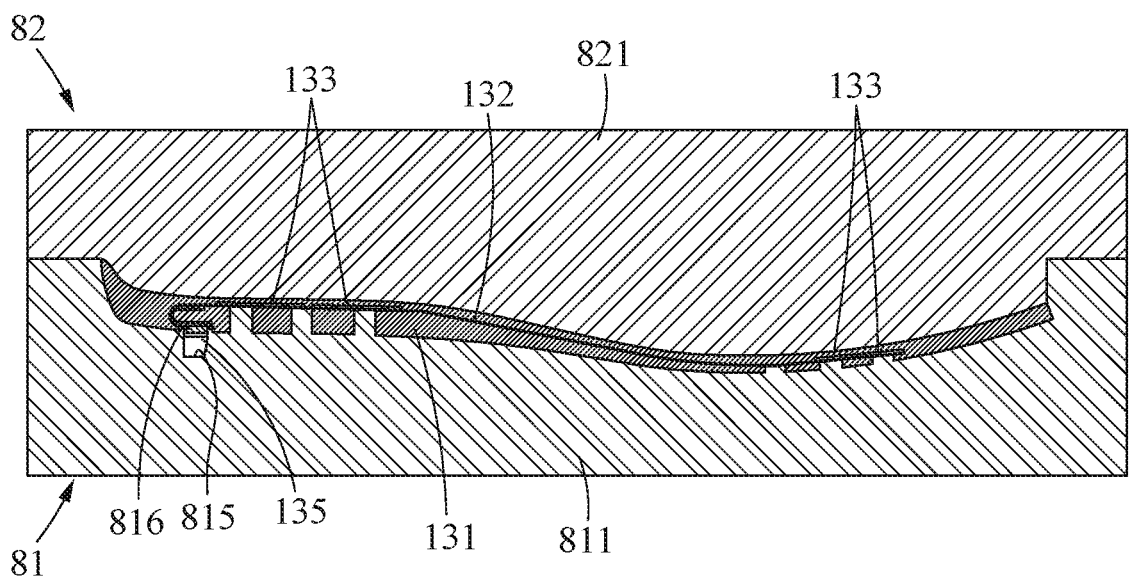
FIG. 22 is a cross-sectional view illustrating a state in which a foam material is foamed in a state in which a support layer is provided between a lower mold frame and an upper mold frame according to at least one example embodiment.

FIG. 19 is a perspective view illustrating a lower mold frame for manufacturing an insole according to at least one example embodiment, FIG. 20 is a perspective view illustrating a state in which a support layer is provided to a lower mold frame according to at least one example embodiment, FIG. 21 is a cross-sectional view illustrating a state in which a lower mold frame, a support layer, and an upper mold frame are separate according to at least one example embodiment, and FIG. 22 is a cross-sectional view illustrating a state in which a foam material is applied in a state in which a support layer is provided between a lower mold frame and an upper mold frame according to at least one example embodiment.

Referring to FIGS. 19 through 22, a lower mold frame 81 and an upper mold frame 82 may assist the insole 13 (see FIG. 2) to embed the electronic element 133 at an exact location. For easy manufacturing, at least one of the lower mold frame 81 and the upper mold frame 82 may be in a structure in which a plurality of frames is stacked.

The lower mold frame 81 may include a lower mold body 811, a bottom surface 812, a first support bar 813, a second support bar 814, and a connector receiving portion 815.

The lower mold body 811 may provide a space for foaming of a foam material.

The bottom surface 812 may be a recessed portion as an outer shape of the insole 13 in the lower mold body 811. The bottom surface 812 may determine an outer shape of a lower side of the insole 13.

The first support bar 813 may protrude from the bottom surface 812 and may support the support layer 132. The first support bars 813 may have a flat top surface, and may include first front support bars 813a provided in a front portion of the lower mold frame 81 and first rear support bars 813b provided in a rear portion of the lower mold frame 81. A height of the first front support bar 813a may be less than that of the first rear support bar 813b. The first support bar 813 may overlap the electronic element 133 in a protruding direction. For example, the first support bar 813 may support a centroid of the electronic element 133.

The first support bar 813 may accurately locate a vertical location of the electronic element 133. Once a distance between the electronic element 133 and the sole of the user is determined to apply appropriate noise to the sole of the user, the first support bar 813 may set a distance from the top surface of the insole 13 to the electronic element 133, which may lead to setting an interval between the foot of the user and the electronic element 133.

Also, the second support bar 814 may support the support layer 132. The second support bar 814 may serve to support the support layer 132 and, at the same time, to inhibit (or, alternatively, prevent) separation of the support layer 132. The second support bars 814 may include second front support bars 814a provided in the front portion of the lower mold frame 81 and second rear support bars 814b provided in the rear portion of the lower mold frame 81. A height of the second front support bar 814a may be less than that of the second rear support bar 814b. The second support bar 814 may include a support bar body 8141 configured to protrude from the bottom surface 812 and a through protrusion 8142 formed on the support bar body 8141.

The support bar body 8141 may be used to set a distance from the bottom surface 812 to the electronic element 133.

The through protrusion 8142 may penetrate the support layer 132 and may set an accurate horizontal location of the electronic element 133. The support layer 132 may include openings each configured to receive the through protrusion 8142. A sectional area of the through protrusion 8142 may be less than that of the support bar body 8141. For example, a cross-sectional area of the through protrusion 8142 may be less than that of the support bar body 8141. The through protrusion 8142 may protrude from a top surface of the support bar body 8141 and may pass through a corresponding opening of the support layer 132 and may inhibit (or, alternatively, prevent) the support layer 132 from moving horizontally due to foaming of the foam material during the manufacturing process.

The connector receiving portion 815 may fasten the connector 135. The connector receiving portion 815 may be a groove or a hole for receiving the connector 135. The connector receiving portion 815 may include a support edge 816 configured to closely attach on the bottom surface of the connector 135. Dissimilar to the bottom surface 812, the support edge 816 may be in a frame shape with the same size. The support edge 816 may be closely attached on the bottom surface of the connector 135 and may inhibit (or, alternatively, prevent) the foam material from flowing between the support edge 816 and the connector 135.

The upper mold frame 82 may cover the lower mold frame 81. The upper mold frame 82 may include an upper mold body 821 and a protruding portion 822 configured to protrude downward from the upper mold body 821 and to determine an upper shape of the insole 13.

Figure 23:
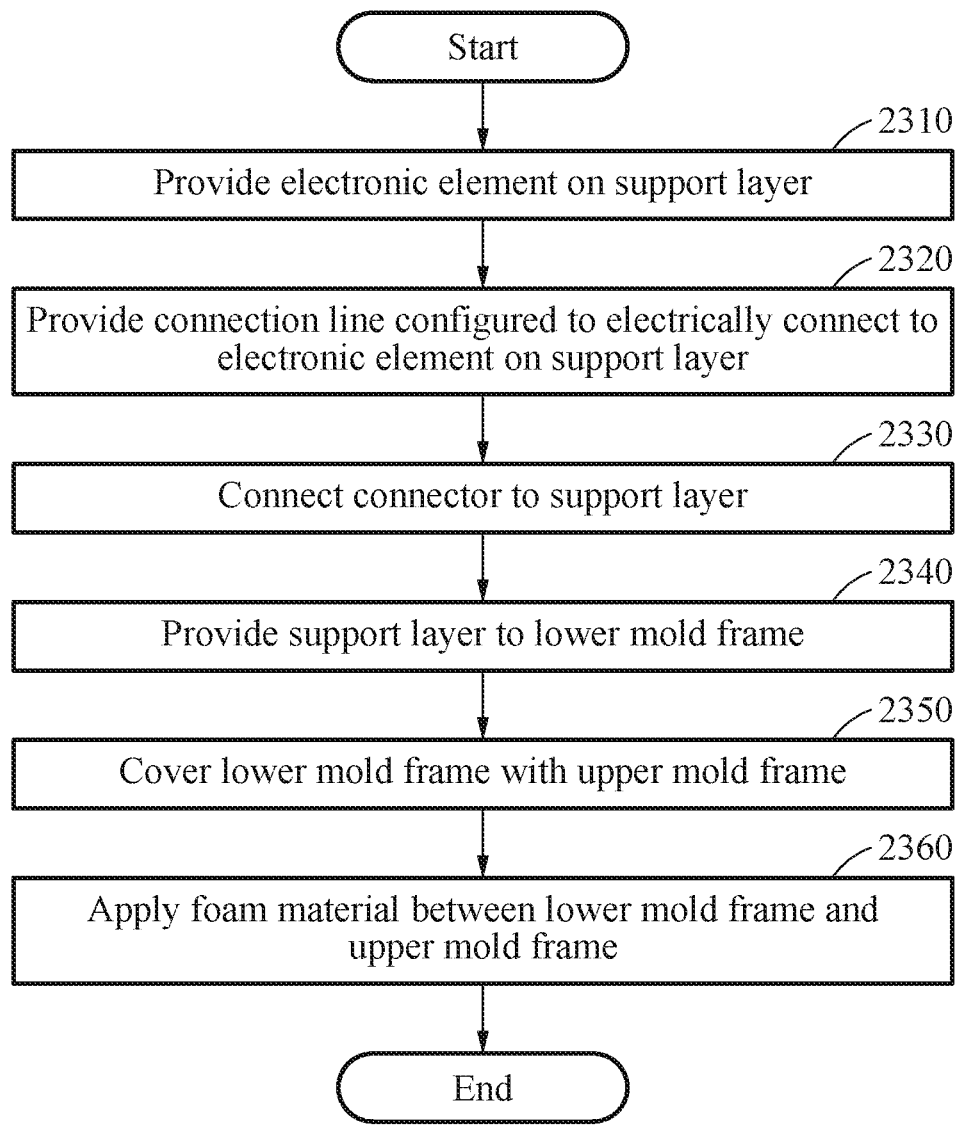
FIG. 23 is a flowchart illustrating an insole manufacturing method according to at least one example embodiment.
Figure 24:
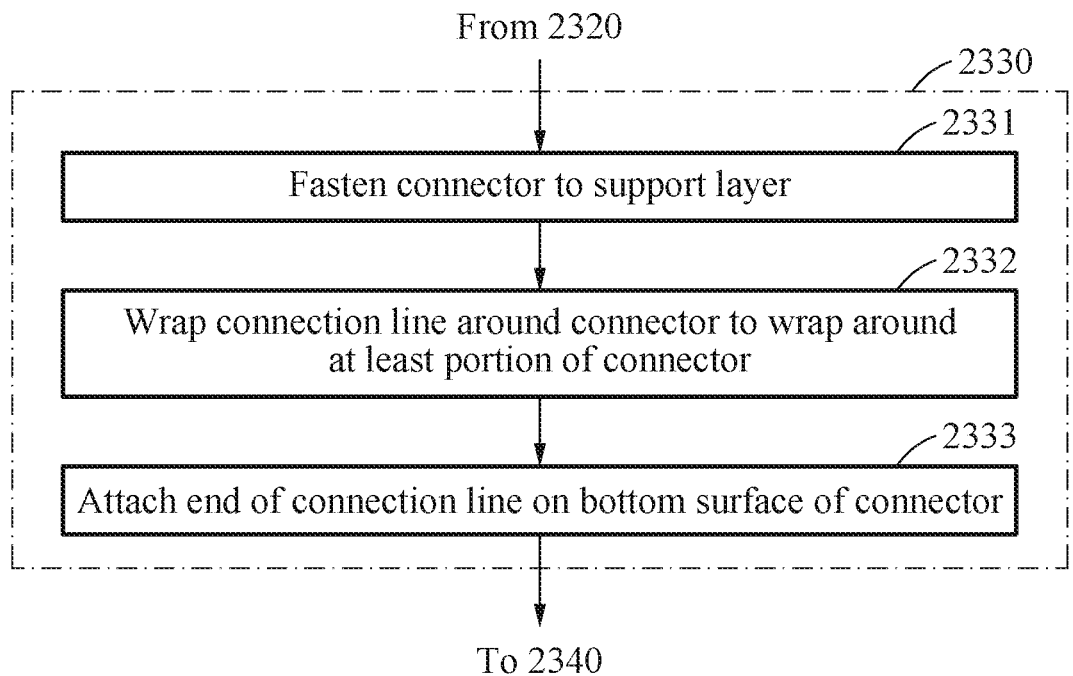
FIG. 24 is a flowchart illustrating an operation of connecting a connector to a support layer according to at least one example embodiment.

FIG. 23 is a flowchart illustrating an insole manufacturing method according to at least one example embodiment, and FIG. 24 is a flowchart illustrating an operation of connecting a connector to a support layer according to at least one example embodiment.

Referring to FIGS. 23 and 24, the insole manufacturing method may include operation 2310 of providing an electronic element on a support layer, operation 2320 of providing a connection line, operation 2330 of connecting a connector to the support layer, operation 2340 of providing the support layer to a lower mold frame, operation 2350 of covering the lower mold frame with an upper mold frame, and operation 2360 of applying a foam material between the lower mold frame and the upper mold frame. Order of each operation illustrated herein is provided as an example only and is not limited thereto unless indicated otherwise.

In operation 2310, the electronic element 133 may be provided on the support layer 132. A plurality of electronic elements 133 may be provided. Operation 2310 may include an operation of arranging a plurality of front electronic elements 133a in a widthwise direction of the support layer 132 on a front portion of the support layer 132. Also, operation 2310 may include an operation of arranging a plurality of rear electronic elements 133b in a lengthwise direction of the support layer 132 on a rear portion of the support layer 132.

In operation 2320, the connection line 134 configured to electrically connect to the electronic element 133 may be provided on the support layer 132.

In operation 2330, the connector 135 may be connected to the support layer 132. For example, the connector 135 may connect to the support layer 132 at a rear end of the support layer 132.

As illustrated in FIG. 24, operation 2330 may include operation 2331 of fastening the connector 135 to the support layer 132, operation 2332 of wrapping the connection line 134 around the connector 135 so that the connection line 134 may wrap around at least a portion of the connector 135, and operation 2333 of attaching an end of the connection line 134 on a bottom surface of the connector 135.

In operation 2340, the support layer 132 may be provided to the lower mold frame 81. The plurality of electronic elements 133 provided on the support layer 132 may be supported by a plurality of support bars 813. The through protrusion 8142 may pass through the support layer 132 and may inhibit (or, alternatively, prevent) the support layer 132 from moving horizontally. For example, when the lower mold frame 81 includes a bottom mold frame 81a and an intermediate mold frame 81b to be assembled (see FIGS. 25 and 26), operation 2340 may include an operation of providing the support layer 132 to the bottom mold frame 81a and an operation of assembling the intermediate mold frame 81b to the bottom mold frame 81a.

In operation 2350, the lower mold frame 81 may be covered with the upper mold frame 82. The lower mold frame 81 and the upper mold frame 82 may engage with each other. A space formed between the lower mold frame 81 and the upper mold frame 82 may not continue to an outside.

In operation 2360, the foam material, for example, poly urethane, may be applied between the lower mold frame 81 and the upper mold frame 82. The foam material applied between the lower mold frame and the upper mold frame may foam in all directions, thereby forming an insole body 131. The insole body 131 may include a first groove that is recessed from a bottom surface of the insole body 131 and has an area greater than an opening formed in the support layer 132. The first groove may be formed by foaming of the foam material in a state in which the support layer 132 is supported by the first support bar 813 of FIG. 19. Also, the insole body 131 may include a second groove that is recessed from the bottom surface of the insole body 131 and has an area less than that of the electronic element. The second groove may be formed by foaming of the foam material in a state in which the support layer 132 is supported by the second support bar 814. Since an area of the second groove is less than that of the electronic element 133, the electronic element 133 may not drop downward.

Figure 25:
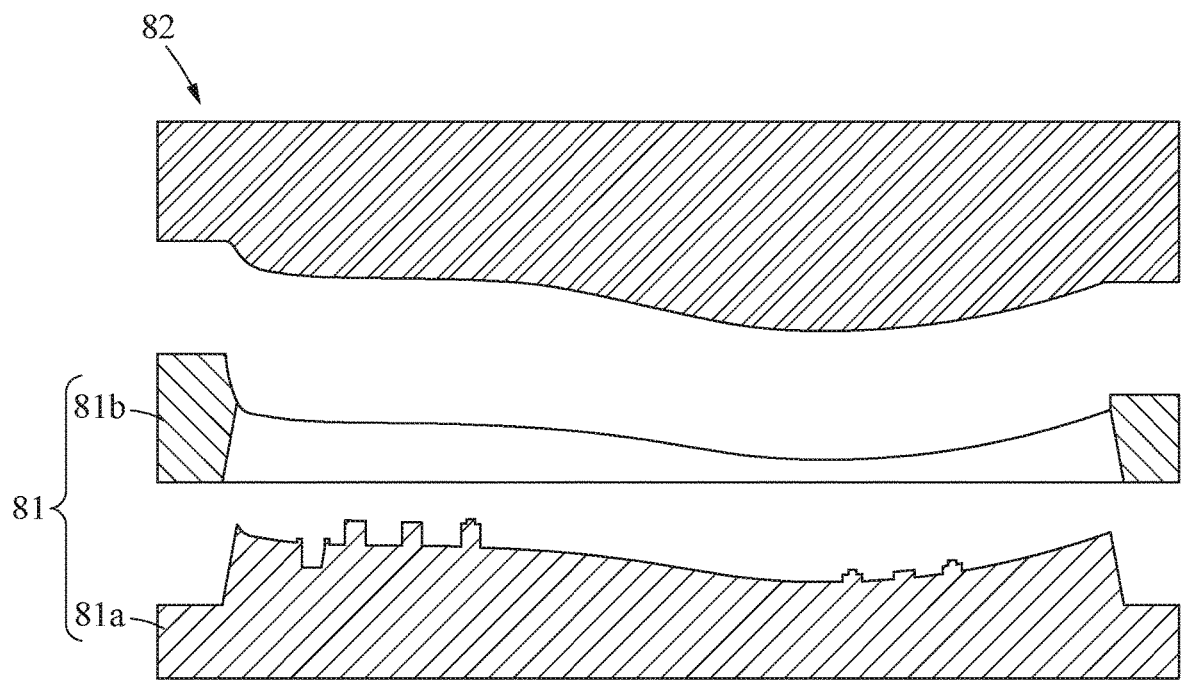
FIG. 25 is a cross-sectional view illustrating a state in which a bottom mold frame, an intermediate mold frame, and an upper mold frame are separate according to at least one example embodiment.
Figure 26:
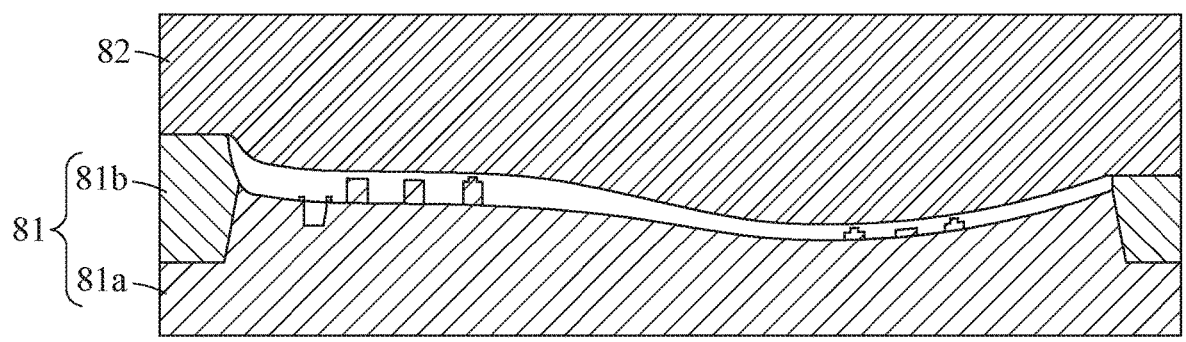
FIG. 26 is a cross-sectional view illustrating a state in which a bottom mold frame, an intermediate mold frame, and an upper mold frame are assembled according to at least one example embodiment.

FIG. 25 is a cross-sectional view illustrating a state in which a bottom mold frame, an intermediate mold frame, and an upper mold frame are separate according to at least one example embodiment, and FIG. 26 is a cross-sectional view illustrating a state in which a bottom mold frame, an intermediate mold frame, and an upper mold frame are assembled according to at least one example embodiment.

Referring to FIGS. 25 and 26, the lower mold frame 81 may include the bottom mold frame 81a and the intermediate mold frame 81b. The bottom mold frame 81a and the intermediate mold frame 81b may be assembled to each other and separate from each other.

The bottom mold frame 81a may support the bottom surface of the support layer 132 (see FIG. 20). The bottom mold frame 81a may include a protruding area for supporting the support layer 132. For example, the protruding area may protrude upward from the bottom mold frame 81a. At least one of the first support bar 813, the second support bar 814, and the connector receiving portion 815 (see FIG. 19) may be provided on the protruding area. Since the support layer 132 is arranged on the protruding area of the bottom mold frame 81a, the support layer 132 may be further accurately received.

The intermediate mold frame 81b may be assembled to the bottom mold frame 81a and may surround the support layer 132 (see FIG. 20). For example, the intermediate mold frame 81b may be in a shape of a ring that may insert into a protruding portion of the bottom mold frame 81a. An inner wall of the intermediate mold frame 81b may surround the support layer 132. A manufacturer may safely place the support layer 132 on the bottom mold frame 81a and then may assemble the intermediate mold frame 81b to the bottom mold frame 81a.

Once the intermediate mold frame 81b is assembled to the bottom mold frame 81a, the intermediate mold frame 81b may be covered with the upper mold frame 82. The insole 13 may be manufactured in a manner that the foam material foams in a space formed by the bottom mold frame 81a, the intermediate mold frame 81b, and the upper mold frame 82. Once the insole 13 is manufactured, the manufacturer may easily take out the manufactured insole 13 by separating the upper mold frame 82 from the intermediate mold frame 81b and by separating the intermediate mold frame 81b from the bottom mold frame 81a.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An insole comprising:
   an insole body insertable in a shoe;
   an electronic element in the insole body;

a connection line configured to be electrically connected to the electronic element, the connection line including a contact terminal exposed to an outside of the insole body; and a connector including,
arms configured to at least partially protrude from a bottom surface of the insole body towards a midsole of the shoe when the insole is inserted in the shoe, and
a base configured to support the contact terminal, and to expose the contact terminal at a portion in which the contact terminal wraps around the base, the base including a lower plate, an upper plate configured to be separated from the lower plate in a vertical direction, and a bridge configured to connect the lower plate and the upper plate, wherein
the arms are configured to protrude downward from the base with respect to a top surface of the insole body.

2. The insole of claim 1, wherein the electronic element comprises:
one or more of a vibrator, a pressure sensor, or an inertial sensor.

3. The insole of claim 1, further comprising:
a support layer in the insole body, the support layer configured to support the electronic element.

4. The insole of claim 1, wherein the arms comprise:
a left arm protruding from a first side of the base with respect to the top surface of the insole body; and
a right arm protruding from a second side of the base with respect to the top surface of the insole body such that the right arm is separated from and faces the left arm.

5. The insole of claim 1, wherein the base is in a U shape that is convex in a direction towards a heel end of the insole.

6. The insole of claim 1, wherein the connection line is configured to attach to a bottom surface of the lower plate with respect to the top surface of the insole body such that the connection line is exposed to the outside of the insole body.

7. The insole of claim 1, wherein the base further comprises:
a plurality of ribs configured to protrude from the lower plate with respect to the top surface of the insole body, the plurality of ribs extending in parallel, and
wherein the connection line is between two adjacent ribs among the plurality of ribs.

8. The insole of claim 1, wherein the base includes a fluid through hole therein in a lengthwise direction of the insole body.

9. The insole of claim 1, wherein the electronic element includes a plurality of electronic elements, the plurality of electronic elements including a first front electronic element and a second front electronic element in a front portion of the insole body, the first front electronic element being spaced apart from the second front electronic element in a widthwise direction of the insole body.

10. The insole of claim 1, wherein the electronic element includes a plurality of electronic elements, the plurality of electronic elements including a first rear electronic element and a second rear electronic element in a rear portion of the insole body, the first rear electronic element being spaced apart from the second rear electronic element in a lengthwise direction of the insole body.

11. A shoe comprising:
a midsole including a receiving groove;
a control device configured to mount to the receiving groove; and
an insole including,
an insole body insertable into an upper portion of the midsole,
an electronic element in the insole body,
a connection line configured to electrically connect to the electronic element, the connection line including a contact terminal exposed to an outside of the insole body, and
a connector configured to connect the connection line to the control device, the connector including,
a base configured to support the contact terminal, and to expose the contact terminal at a portion in which the contact terminal wraps around the base, the base including a lower plate, an upper plate configured to be separated from the lower plate in a vertical direction, and a bridge configured to connect the lower plate and the upper plate, wherein
arms are configured to protrude downward from the base with respect to a top surface of the insole body.

12. The shoe of claim 11, wherein the electronic element comprises:
one or more of a vibrator, a pressure sensor, or an inertial sensor.

13. The shoe of claim 11, wherein the insole further comprises:
a support layer in the insole body, the support layer configured to support the electronic element.

14. The shoe of claim 13, wherein the support layer has a hole therein, and
the insole body has a groove recessed in a bottom surface of the insole body, the groove having an area greater than that of the hole.

15. The shoe of claim 11, wherein at least a portion of the connector is configured to protrude from the insole body towards the outside of the insole body.

16. The shoe of claim 11, wherein the control device comprises:
a case including a fastening groove configured to receive a portion of the connector; and
an access terminal in an upper portion of the case, the access terminal configured to contact the connection line.

17. The shoe of claim 16, wherein the access terminal is configured to move in a vertical direction relative to a top surface of the case.

18. The shoe of claim 11, wherein the insole body has a groove recessed in a bottom surface of the insole body, the groove having an area less than that of the electronic element.

* * * * *